(12) United States Patent
Doll et al.

(10) Patent No.: US 6,440,974 B2
(45) Date of Patent: Aug. 27, 2002

(54) COMPOUNDS USEFUL FOR INHIBITION OF FARNESYL PROTEIN TRANSFERASE

(75) Inventors: Ronald J. Doll, Maplewood; Carmen Alvarez, Roselle Park; Tarik Lalwani, Edison; Yi-Tsung Liu, Morris Township, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/788,947

(22) Filed: Feb. 20, 2001

Related U.S. Application Data

(62) Division of application No. 09/447,491, filed on Nov. 23, 1999, now Pat. No. 6,228,865, which is a continuation of application No. 09/094,686, filed on Jun. 15, 1998, now abandoned.
(60) Provisional application No. 60/049,951, filed on Jun. 17, 1997.

(51) Int. Cl.$^7$ .................... A61K 31/496; C07D 403/14; C07D 409/14; A61P 35/00
(52) U.S. Cl. .................... 514/253.03; 544/361; 544/59; 544/121; 514/232.8; 514/228.2
(58) Field of Search .................... 544/361, 59, 121; 514/253.03, 232.8, 228.2

(56) References Cited

U.S. PATENT DOCUMENTS

| | | |
|---|---|---|
| 4,826,853 A | 5/1989 | Piwinski et al. |
| 5,089,496 A | 2/1992 | Piwinski et al. |
| 5,151,423 A | 9/1992 | Piwinski et al. |
| 5,393,890 A | 2/1995 | Syoji et al. |
| 5,661,152 A | 8/1997 | Bishop et al. |
| 5,672,611 A | 9/1997 | Doll et al. |
| 5,684,013 A | 11/1997 | Afonso et al. |
| 5,696,121 A | 12/1997 | Bishop et al. |
| 5,700,806 A | 12/1997 | Doll et al. |
| 5,703,090 A | 12/1997 | Afonso et al. |
| 5,712,280 A | 1/1998 | Doll et al. |
| 5,714,609 A | 2/1998 | Bishop et al. |
| 5,719,148 A | 2/1998 | Bishop et al. |
| 5,721,236 A | 2/1998 | Bishop et al. |
| 5,728,703 A | 3/1998 | Bishop et al. |
| 6,277,854 B1 * | 8/2001 | Njoroge ..................... 514/254 |

FOREIGN PATENT DOCUMENTS

| | | |
|---|---|---|
| EP | 0270818 | 6/1988 |
| EP | 396083 | 11/1990 |
| WO | 0495484 | 7/1992 |
| WO | WO95/10515 | 4/1995 |
| WO | WO95/10516 | 4/1995 |
| WO | WO95/15949 | 6/1995 |
| WO | WO96/30018 | 10/1996 |
| WO | WO96/30362 | 10/1996 |
| WO | WO96/30363 | 10/1996 |
| WO | WO96/31477 | 10/1996 |
| WO | WO96/31478 | 10/1996 |
| WO | WO97/23478 | 7/1997 |
| WO | WO 98 11092 | 3/1998 |

OTHER PUBLICATIONS

Khosravi–Far R et al. Cell Growth & Differentiation. 3, 461–468 (1992).*
Bishop et al., The Journal of Biological Chemistry, vol. 270, No. 15, pp. 30611–30618 (1995).
Njoroge et al., Bioorganic & Medicinal Chemistry Letters, vol. 6, No. 24, pp. 2977–2982 (1996).

* cited by examiner

*Primary Examiner*—Evelyn Mei Huang
(74) *Attorney, Agent, or Firm*—Robert L. Bernstein

(57) ABSTRACT

Novel compounds of the formula:

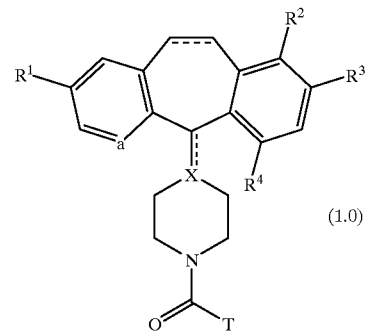

(1.0)

are disclosed. In Formula 1.0 a represents N or NO, $R^1$ and $R^3$ are halo, $R^2$ and $R^4$ are independently H or halo provided that at least one is H, X is C, CH or N, and T represents a five or six membered heterocycloalkyl ring having one or two heteroatoms selected from S or O.

Also disclosed are methods of inhibiting farnesyl protein transferase and methods for treating tumor cells.

9 Claims, No Drawings

COMPOUNDS USEFUL FOR INHIBITION OF FARNESYL PROTEIN TRANSFERASE

REFERENCE TO RELATED APPLICATIONS

This application is a divisional of application Ser. No. 09/447,491 filed Nov. 23, 1999 now U.S. Pat. No. 6,228,865 which is a continuation of application Ser. No. 09/094,686 filed Jun. 15, 1998 abandoned, which claims the benefit of U.S. Provisional Application Ser. No. 60/049,951 filed Jun. 17, 1997.

BACKGROUND

WO 95/10516, published Apr. 20, 1995 discloses tricyclic compounds useful for inhibiting farnesyl protein transferase.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds useful for the inhibition of farnesyl protein transferase (FPD. The compounds of this invention are represented by the formula:

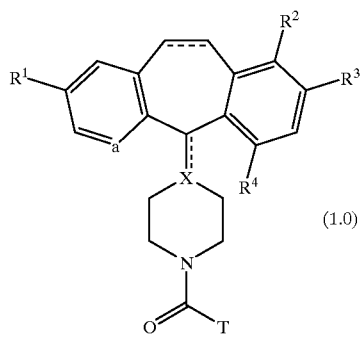

(1.0)

or a pharmaceutically acceptable salt or solvate thereof, wherein:

a represents N or NO⁻;

$R^1$ and $R^3$ are the same or different halo atom;

$R^2$ and $R^4$ are selected from H and halo, provided that at least one of $R^2$ and $R^4$ is H;

the dotted line (---) represents an optional bond;

X is N, C when the optional bond is present, or CH when the optional bond is absent;

T is a substituent selected from:

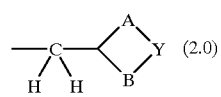

(2.0)

wherein:

A represents $-(CH_2)_b-$;

B represents $-(CH_2)_d-$;

b and d are independently selected from: 0, 1, 2, 3, or 4 such that the sum of b and d is 3 or 4; and Y is selected from: O, S, SO, or $SO_2$;

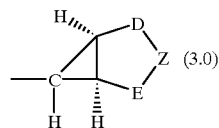

(3.0)

wherein:

D represents $-(CH_2)_e-$;

E represents $-(CH_2)_f-$;

e and f are independently selected from: 0, 1, 2, or 3 such that the sum of e and f is 2 or 3; and Z is O;

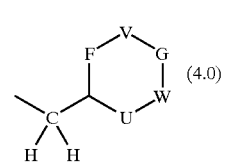

(4.0)

wherein:

F represents $-(CH_2)_g-$;

G represents $-(CH_2)_h-$;

U represents $-(CH_2)_i-$;

h represents 1, 2, or 3 g and i are independently selected from: 0, 1 or 2 such that the sum of h, g and i is 2 or 3; and V and W are independently selected from O, S, SO, or $SO_2$;

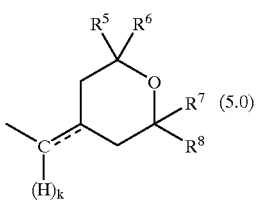

(5.0)

wherein:

the dotted line (---) represents an optional bound:

k is 1 or 2 such that when the optional bond is present k represents 1, and when the optional double bond is absent then k represents 2;

$R^5$, $R^6$, $R^7$ and $R^8$ are the same alkyl (preferably methyl); or $R^5$ and $R^7$ are the same alkyl (preferably methyl), and $R^6$ and $R^8$ are H;

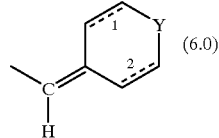

(6.0)

wherein:

the dotted lines (---) represent optional bonds 1 and 2 such that optional bonds 1 and 2 are both present, or optional bonds 1 and 2 are both absent;

Y represents O, S, SO, or $SO_2$;

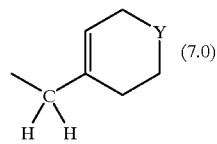
(7.0)

wherein:

Y represents O, S, SO, or $SO_2$;

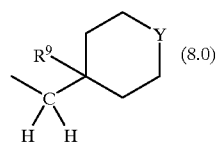
(8.0)

wherein:

$R^9$ is selected from: —CN, —$CO_2H$, or —C(O)N($R^{10}$)$_2$;

each $R^{10}$ is the same or diferent alkyl group (preferably, methyl);

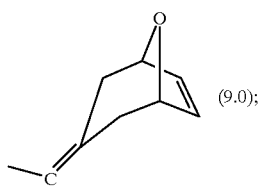
(9.0);

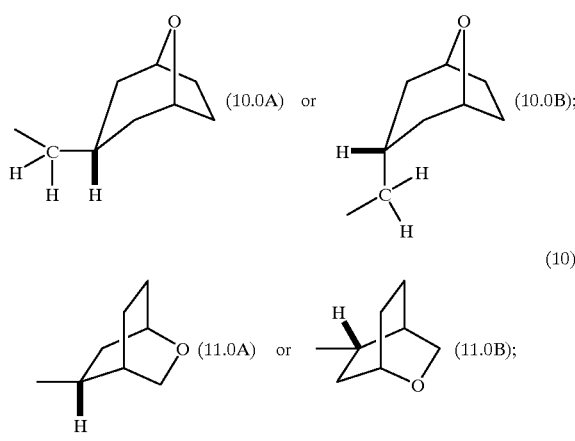

Isomer 1      Isomer 2

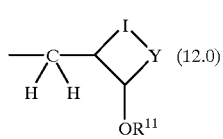
(12.0)

wherein:

I represents —(CH$_2$)$_m$—;

m represents 2 or 3;

Y represents O, S, SO, or $SO_2$; and $R^{11}$ represents alkyl (preferably ethyl);

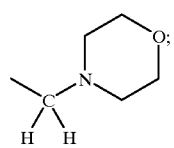

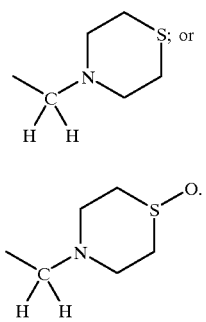

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount of the tricyclic compounds described above. The administration of the compounds of this invention to patients, to inhibit farnesyl protein transferase, is useful in the treatment of the cancers described below.

This invention provides a method for inhibiting or treating the abnormal growth of cells. including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of the tricyclic compounds, described herein, to a mammal (e.g., a human) in need of such treatment. In particular, this invention provides a method for inhibiting or treating the growth of tumors expressing an activated Ras oncogene by the administration of an effective amount of the above described compounds. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The tricyclic compounds useful in the methods of this invention inhibit or treat the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

$MH^+$—represents the molecular ion plus hydrogen of the molecule in the mass spectrum:

Et (or ET)—represents ethyl ($C_2H_5$);

alkyl—represents straight and branched carbon chains and contains from one to twenty carbon atoms, preferably one to six carbon atoms;

halo-represents fluoro, chloro, bromo and iodo;

The following solvents and reagents are referred to herein by the abbreviations indicated: ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); 1-(3-dimethylaminopropyl)-3-ethyl carbodiimide hydrochloride (DEC); diisobutylaluminum hydride(DIBAL); and 4-methylmorpholine (NMM).

The positions in the tricyclic ring system are:

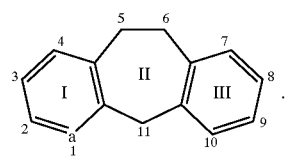

Preferred halo atoms for $R^1$, $R^2$, $R^3$, and $R^4$ in Formula 1.0 are selected from: Br, Cl or I, with Br and Cl being preferred.

Compounds of Formula 1.0 include compounds of the formula:

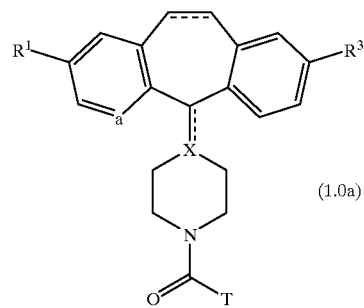

(1.0a)

wherein $R^1$ and $R^3$ are the same or different halo. Preferably, for these dihalo compounds, $R^1$ and $R^3$ are independently selected from Br or Cl, and more preferably $R^1$ is Br and $R^3$ is Cl. Preferably, X is CH or N, with CH being more preferred.

Compounds of Formula 1.0 include compounds of Formulas 1.1 and 1.2:

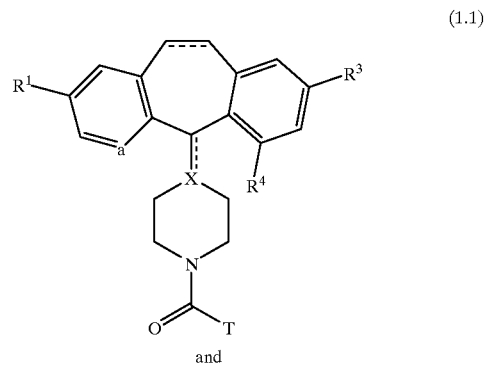

(1.1)

and

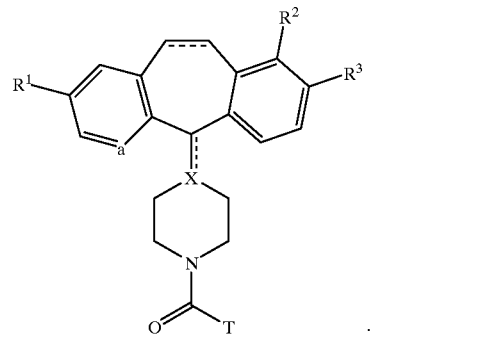

(1.2)

wherein $R^1$, $R^3$ and $R^4$ in Formula 1.1 are halo, and $R^1$, $R^2$ and $R^3$ in Formula 1.2 are halo. Compounds of Formula 1.1 are preferred.

Preferably, in Formula 1.1, $R^1$ is Br, $R^3$ is Cl, and $R^4$ is halo. More preferably, in Formula 1.1, $R^1$ is Br, $R^3$ is Cl, and $R^4$ is Br.

Preferably, in Formula 1.2, $R^1$ is Br, $R^2$ is halo, and $R^3$ is Cl. More preferably, in Formula 1.1, $R^1$ is Br, $R^2$ is Br, and $R^3$ is Cl.

Preferably, for compounds of Formulas 1.1 and 1.2, X is CH or N. For compounds of Formula 1.1, X is preferably CH.

Preferably, for the compounds of this invention, the optional bond between positions 5 and 6 (i.e., C5–C6) in the tricyclic system is absent.

Also, preferably, for the compounds of this invention, substituent a in Ring I represents N.

Those skilled in the art will appreciate that compounds of Formula 1.0 include compounds of Formulas 1.3 and 1.4:
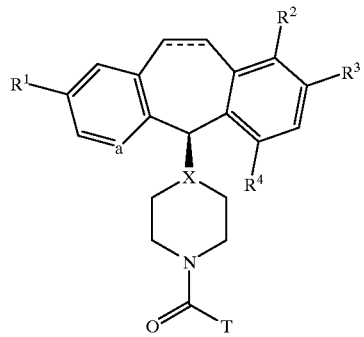
(1.3)
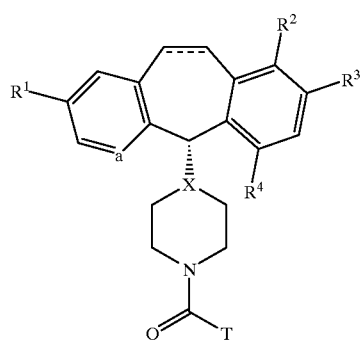
(1.4)
wherein X is CH or N, with compounds of 1.3 being preferred for compounds of Formula 1.1, and with compounds of Formula 1.4 being preferred for componds of Formula 1.2.
Thus, compounds of the invention include compounds of the formulas:
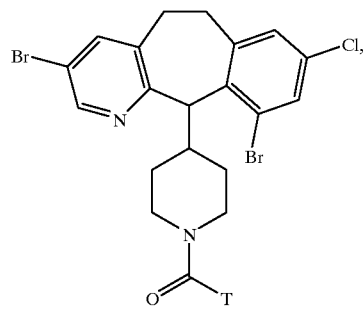
(1.5)
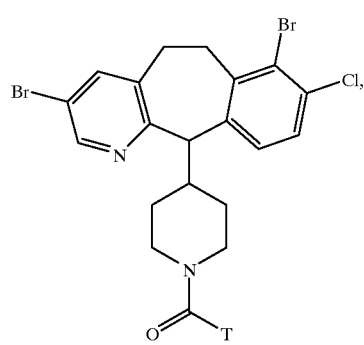
(1.6)
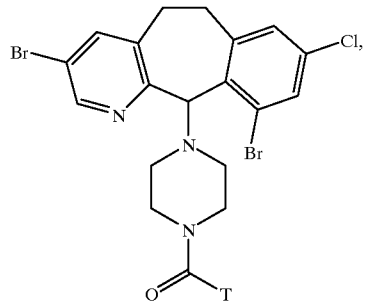
(1.7)
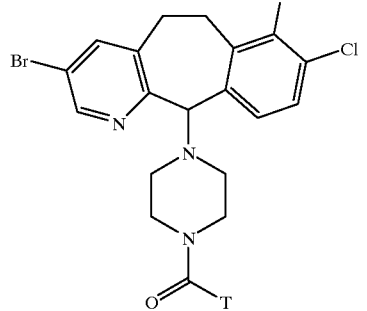
(1.8)
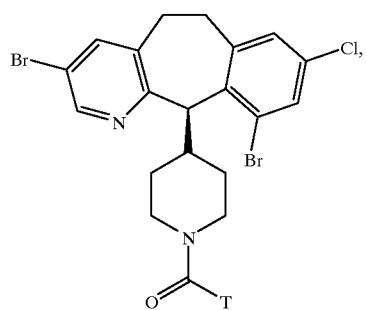
(1.9)
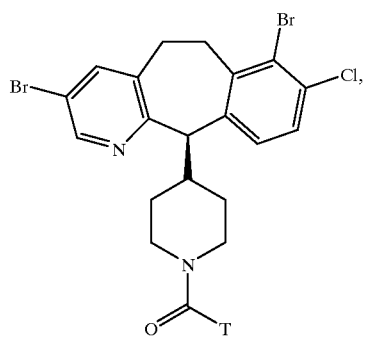
(1.10)
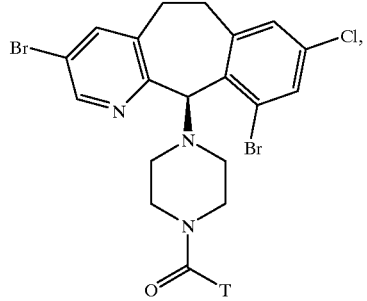
(1.11)

(1.12)
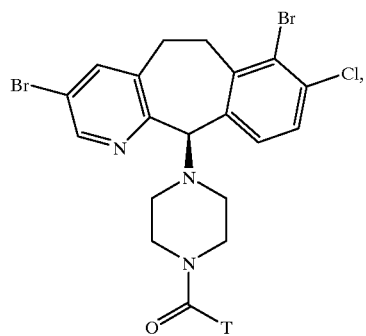

(1.13)
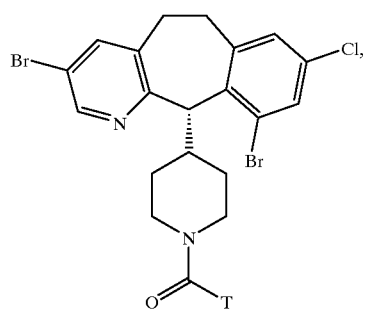

(1.14)
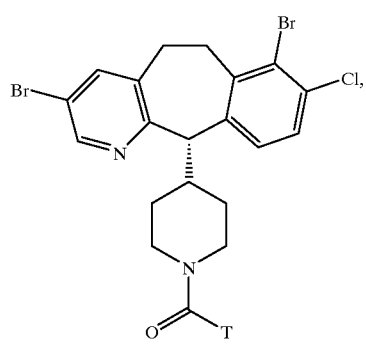

(1.15)
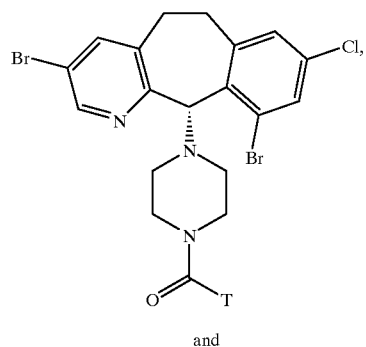

and (1.16)
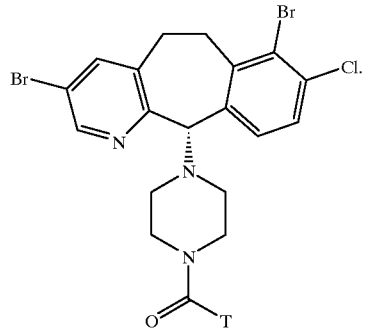

Compounds of Formula 1.9 are preferred.
Preferably substituent T is (2.0)
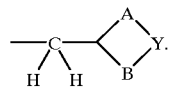

More preferably, substituent T is the substituent of Formula 2.0 wherein the sum of b and d is 4. Most preferably b is 2 and d is 2 forming the group:

(2.1)
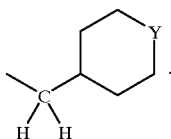

Preferably, Y is O.

Examples of Formula 2.0 also include substituents wherein: (a) the sum of b and d is 3, wherein b is 3 and d is 0; (b) the sum of b and d is 4, wherein b is 4 and d is 0; (c) the sum of b and d is 4, wherein b is 3 and d is 1; and (d) the sum of b and d is 3, wherein b is 2 and d is 1. For these examples Y is preferably O.

Examples of Formula 2.0 include:

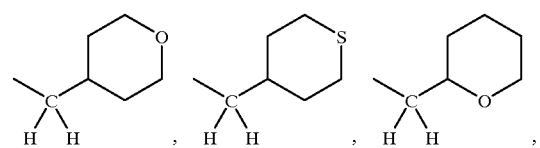

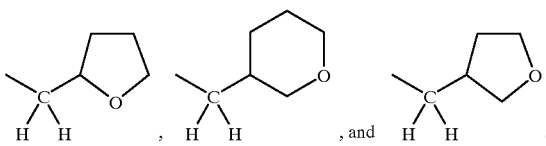

Formula 3.0

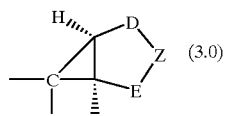
(3.0)

includes substituents wherein: (a) the sum of e and f is 3, wherein e is 3 and f is 0; (b) the sum of e and f is 2, wherein e is 1 and d is 1; and (c) the sum of e and f is 2, wherein e is 2 and f is 0.

Examples of Formula 3.0 include:

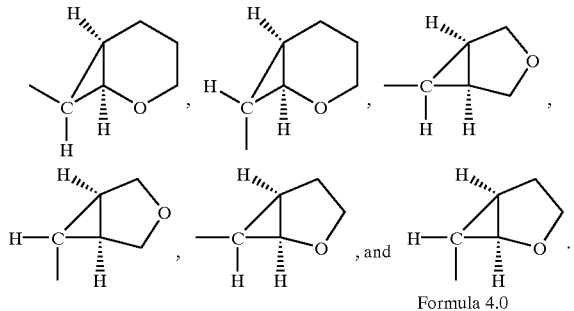

Formula 4.0

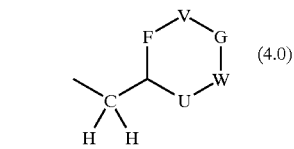

includes substituents wherein: g is 0, h is 2, and i is 1. Preferably, V and W are O. For example, Formula 4.0 includes the substituent

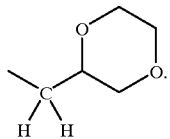

Formula 5.0

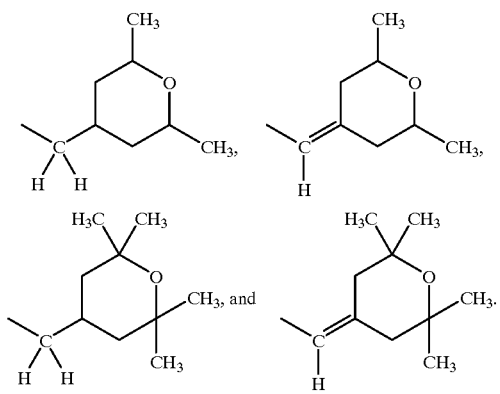

includes the substituents:

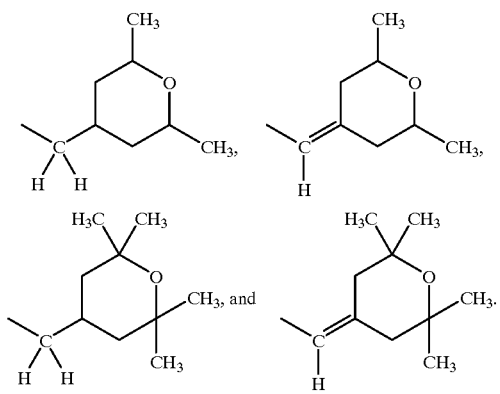

Formula 6.0

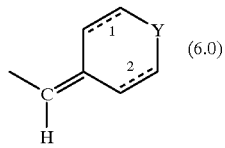

includes the substituents:

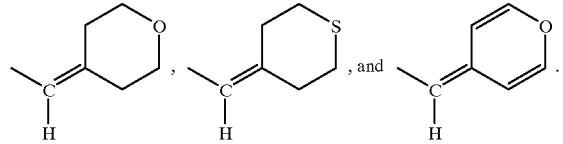

Representative compounds of the invention include compounds of the formula:

(1.16)

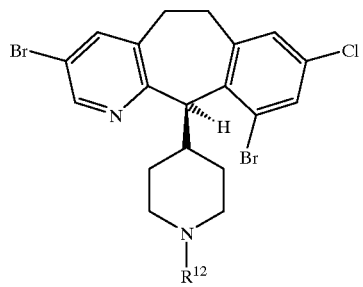

wherein $R^{12}$ is selected from:

(1)

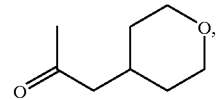

(2)

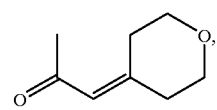

(3)

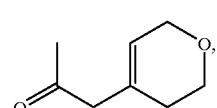

(4)

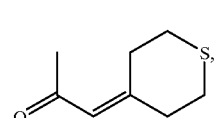

(5)

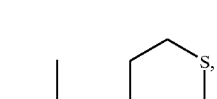

-continued
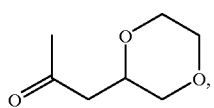 (6)
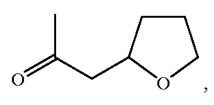 (7)
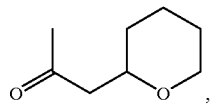 (8)
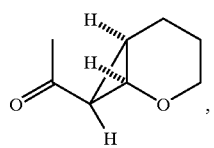 (9)
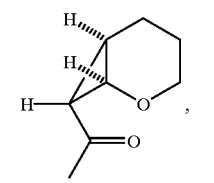 (10)
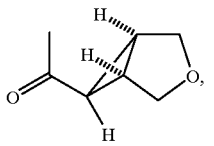 (11)
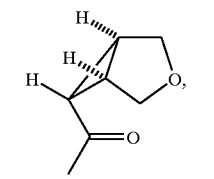 (12)
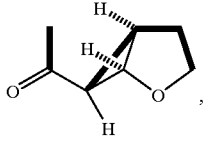 (13)
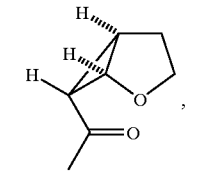 (14)
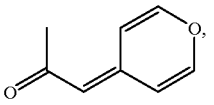 (15)
-continued
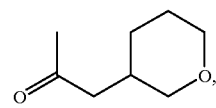 (16)
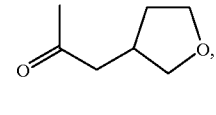 (17)
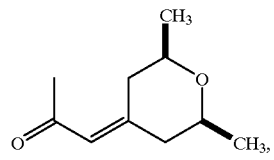 (18)
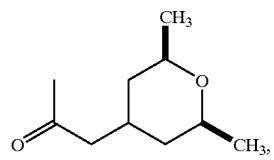 (19)
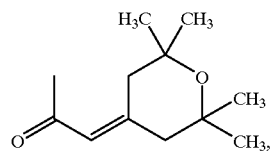 (20)
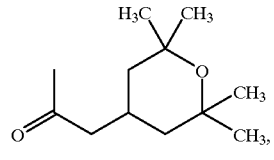 (21)
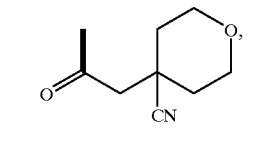 (22)
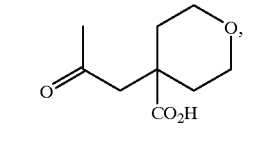 (23)
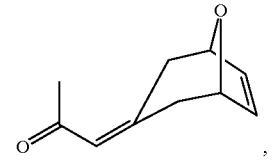 (24)
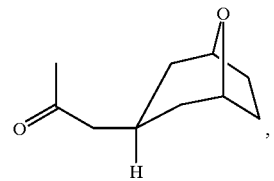 (25)

(26) 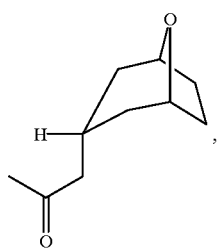
(27) 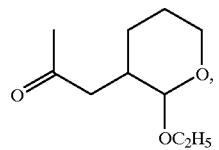
(28) 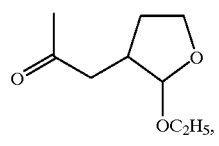
(29) 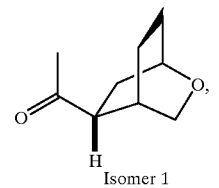
Isomer 1
(30) 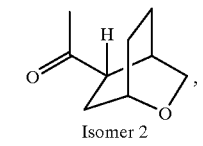
Isomer 2
(31) 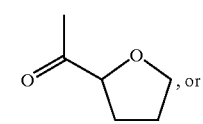, or
(32) 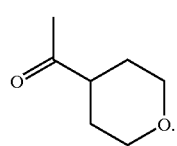
(33) 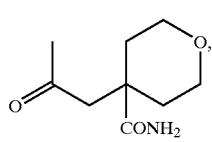
(34) 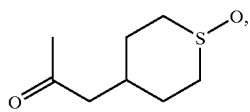
(35) 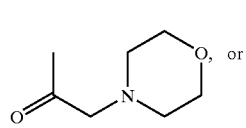, or
(36) 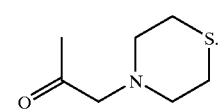
Those skilled in the art will appreciate that substituent $R^{12}$ is the same as substituent
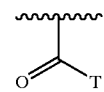
in Formula 1.0.
Representative compounds of this invention also include:
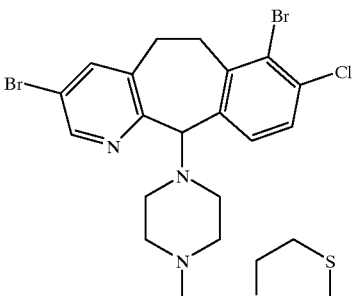
and
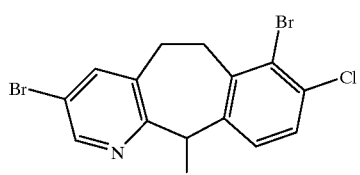
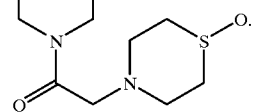

Representative compounds of the invention also include:

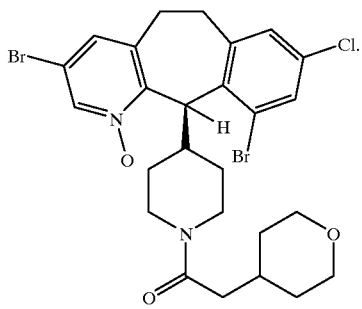

Lines drawn into the ring systems indicate that the indicated bond may be attached to any of the substitutable ring carbon atoms.

Certain compounds of the invention may exist in different isomeric (e.g., enantiomers and diastereoisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines. hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of the invention may be prepared according to the procedures described in WO 95/10516 published Apr. 20, 1995, U.S. Pat. No. 5,719,148 issued Feb. 17, 1998, and copending application Ser. No. 08/766,601 filed Dec. 12, 1996; the disclosures of each being incorporated herein by reference thereto; and according to the procedures described below.

Compounds of the invention can be prepared according to the reaction:

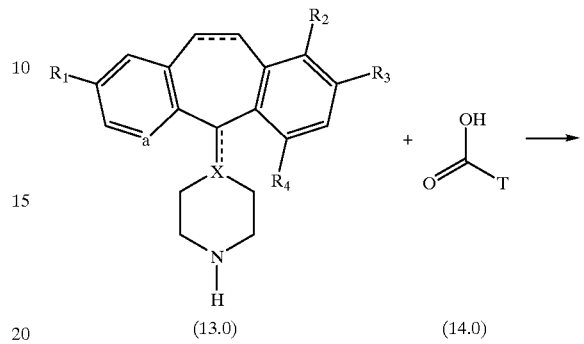

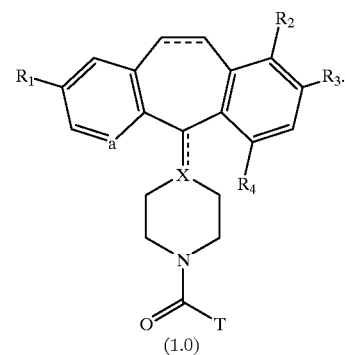

In the reaction, the cyclic ether carboxylic acid (14.0) is coupled to the tricyclic amine (14.0) using amide bond forming conditions well known to those skilled in the art. The substituents are as defined for Formula 1.0. For example, carbodiimide coupling methods (e.g., DEC) can be used. For example, the carboxylic acid (14.0) can be reacted with the tricyclic amine (13.0) using DEC/HOBT/NMM in DMF at about 25° C. for a sufficient period of time, e.g., about 18 hours, to produce a compound of Formula 1.0.

For example, using the carbodiimide coupling methods, compounds of the invention can be produced according to the reaction:

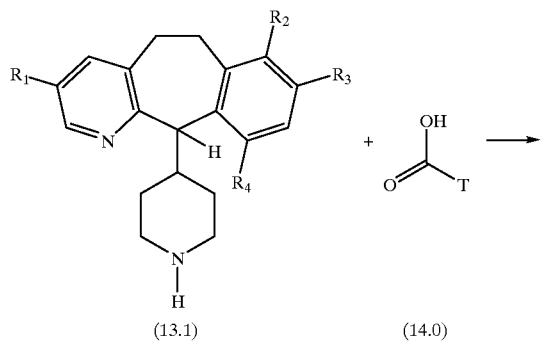

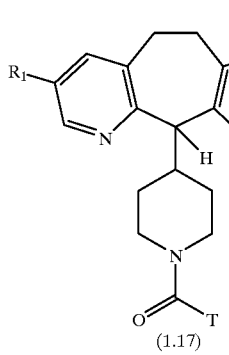

(1.17)

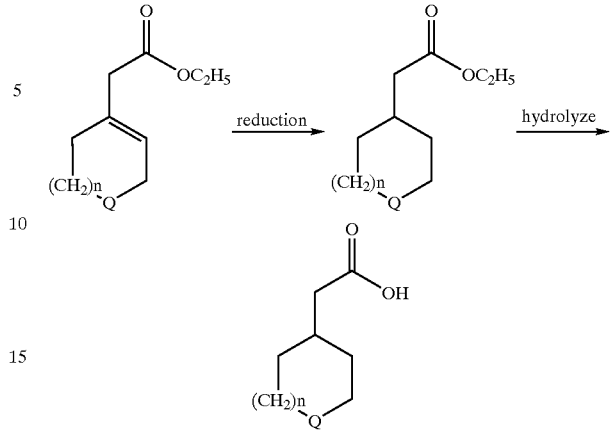

The cyclic ether carboxylic acids (14.0) are prepared by methods well known in the art. Commercially available cyclic ether ketones can be reacted in a Wittig reaction to produce olefinesters. The olefin is then reduced by catalytic hydrogenation or by metal hydride reduction to the saturated cyclic ether acetates which are then hydrolyzed to the cyclic ether acids (14.0). See, for example, J. Med. Chem. (1993), 36, 2300, the disclosure of which is incorporated herein by reference thereto. The reaction is illustrated in Scheme 1 below.

Scheme 1

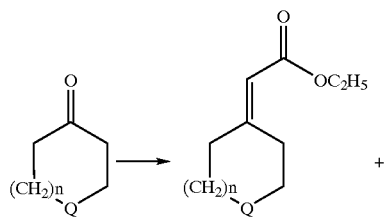

In Scheme 1, n represents 0 or 1, and Q represents O or S.

The exocyclic olefin from the Wittig reaction in Scheme 1 can be reacted with cyanide in a Michael reaction to form a nitrile, or with hydrogen peroxide to form an epoxide. The nitrile can be hydrolyzed to a carboxy group and later converted to amides. The epoxide can be hydrolyzed or reduced to an alcohol. This reaction, well known to those skilled in the art, is illustrated in Scheme 2 below.

Scheme 2

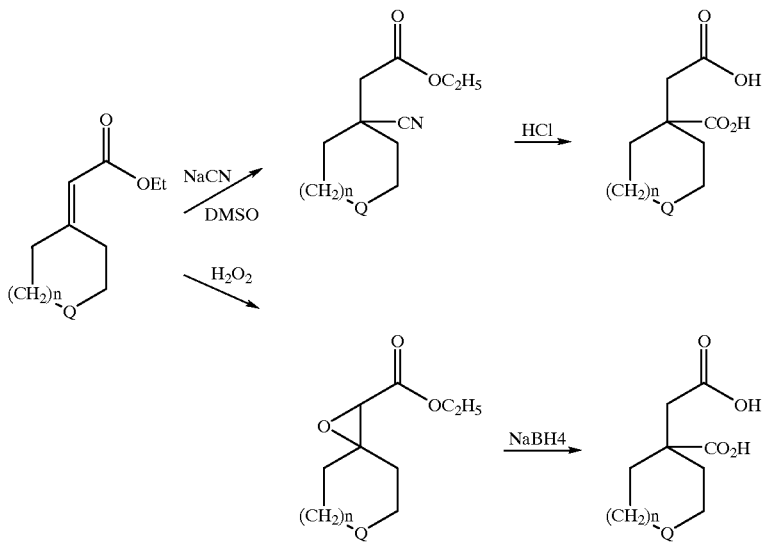

wherein n and Q are as defined in Scheme 1.

The cyclic ether acetates can also be produced by the insertion of an acetate carbene into a C—H bond next to the ether heteroatom of a cyclic ether, as described in Tetrahedron (1989). 45, 69. The acetate carbene can be produced from a diazoacetate, such as ethyl diazoacetate, and a rhodium or copper catalyst, such as dirhodium diacetate of copper sulfate and heat. This is illustrated by the reaction:

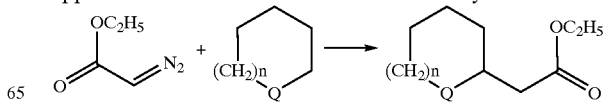

wherein n and Q are as defined in Scheme 1.

If the cyclic ether contains a double bond, the acetate carbene can add to the double bond to produce a bicyclocyclic ether acetate as described in Comp. Rend. (1957), 244, 2806. If the double bond is adjacent to the ether heteroatom, the resulting cyclopropyl ring can be opend by catalytic hydrogenation by an alcohol and acid. This reaction is illustrated in Scheme 3 below.

Scheme 3

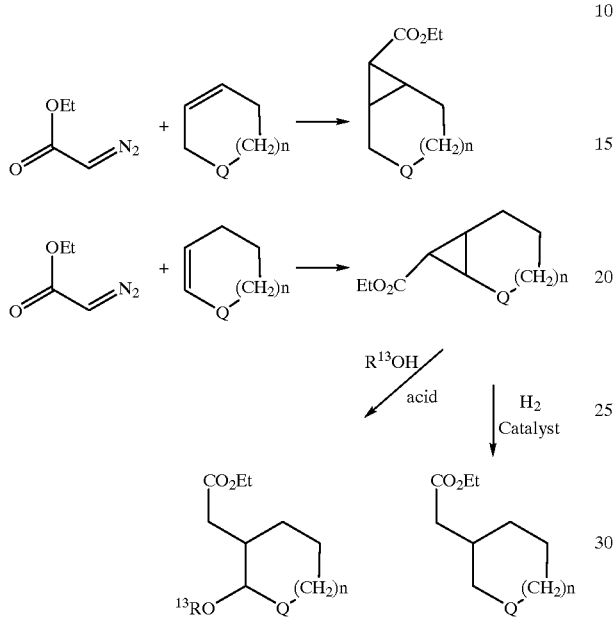

wherein n and Q are as defined in Scheme 1.

Cyclic ethers containing a carboxy group directly attached can be prepared by a base catalyzed cyclization of a dihalo ether with diethyl malonate followed by hydrolysis and decarboxylation as described in J. Am. Chem. Soc. (1995), 115, 8401. This is illustrated by Scheme 4 below.

Scheme 4

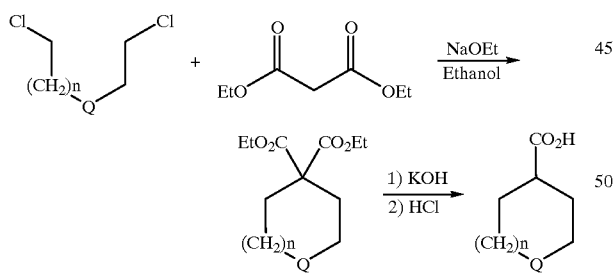

wherein n and Q are as defined in Scheme 1.

Many bicyclic-cyclic ether ketones are known in the literature. Many of these can be made by Deils-Alder processes. For example, J. Am. Chem. Soc. (1978), 100, 1765 describes the the reaction:

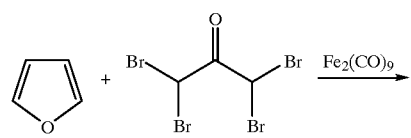

-continued

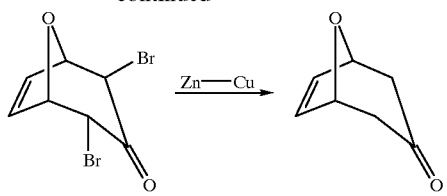

These bicyclic-cyclic ether ketones can be reacted in a Wittig reaction as above to produce bicyclic-cyclic ether acetates.

Compounds of Formula 13.0a (13.0a)

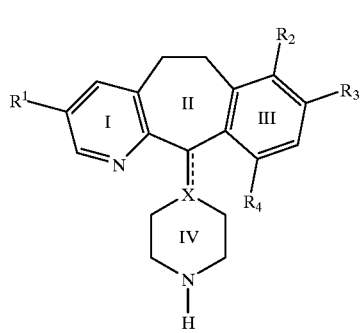

are prepared by methods known in the art, for example by methods disclosed in WO 95/10516, in U.S. Pat. No. 5,151, 423 and those described below. Compounds of Formula 13.0a wherein X is C (when the double bond is present) or CH and the C-3 postion of the pyridine ring in the tricyclic structure is substituted by bromo (i.e., $R^1$ is Br) can also be prepared by a procedure comprising the following steps:

(a) reacting an amide of the formula

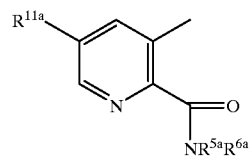

wherein $R^{11a}$ is Br, $R^{5a}$ is hydrogen and $R^{6a}$ is $C_1$–$C_6$ alkyl, aryl or heteroaryl; $R^{5a}$ is $C_1$–$C_6$ alkyl, aryl or heteroaryl and $R^{6a}$ is hydrogen; $R^{5a}$ and $R^{6a}$ are independently selected from the group consisting of $C_1$–$C_6$ alkyl and aryl; or $R^{5a}$ and $R^{6a}$, together with the nitrogen to which they are attached, form a ring comprising 4 to 6 carbon atoms or comprising 3 to 5 carbon atoms and one hetero moiety selected from the group consisting of —O— and —$NR^{9a}$—, wherein $R^{9a}$ is H, $C_1$–$C_6$ alkyl or phenyl;

with a compound of the formula

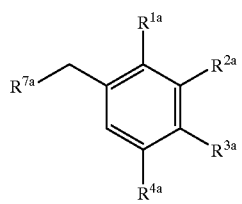

wherein $R^{1a}$, $R^{2a}$, $R^{3a}$ and $R^{4a}$ are are independently selected from the group consisting of hydrogen and halo and $R^{7a}$ is Cl or Br, in the presence of a strong base to obtain a compound of the formula

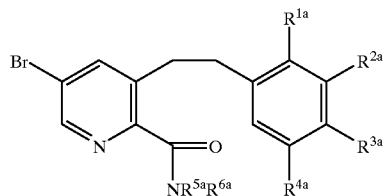

(b) reacting a compound of step (a) with
(i) $POCl_3$ to obtain a cyano compound of the formula

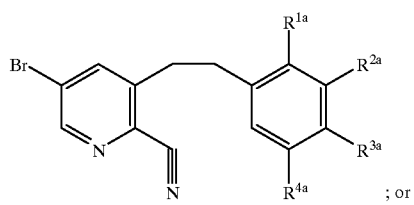

; or (ii) DIBALH to obtain an aldehyde of the formula

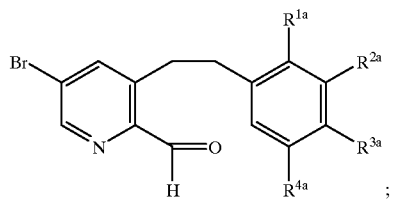

;

(c) reacting the cyano compound or the aldehyde with a piperidine derivative of the formula

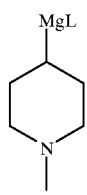

wherein L is a leaving group selected from the group consisting of Cl and Br, to obtain a ketone or an alcohol of the formula below, respectively:

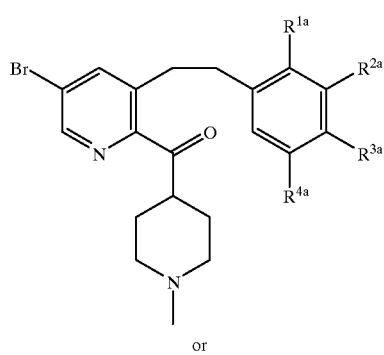

or

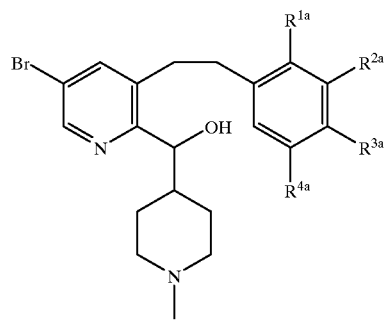

(d)(i) cyclizing the ketone with $CF_3SO_3H$ to obtain a compound of Formula 13.0a wherein the dotted line represents a double bond; or (d)(ii) cyclizing the alcohol with polyphosphoric acid to obtain a compound of Formula 13.0a wherein the dotted line represents a single bond.

Methods for preparing compounds of Formula 13.0a disclosed in WO 95/10516, U.S. Pat. No. 5,151,423 and described below employ a tricyclic ketone intermediate. Such intermediates of the formula

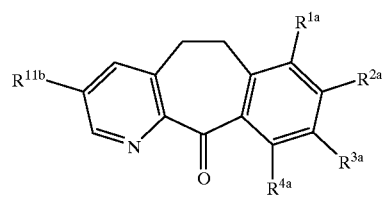

wherein $R^{11b}$, $R^{1a}$, $R^{2a}$, $R^{3a}$ and $R^{4a}$ are independently selected from the group consisting of hydrogen and halo, can be prepared by the following process comprising:

(a) reacting a compound of the formula

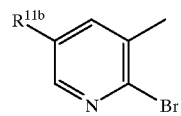

(i) with an amine of the formula $NHR^{5a}R^{6a}$, wherein $R^{5a}$ as $R^{6a}$ are as defined in the process above; in the presence of a palladium catalyst and carbon monoxide to obtain an amide of the formula:

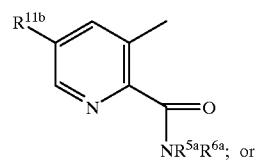

; or (ii) with an alcohol of the formula $R^{10a}OH$, wherein $R^{10a}$ is $C_1$–$C_6$ lower alkyl or $C_3$–$C_6$ cycloalkyl, in the presence of a palladium catalyst and carbon monoxide to obtain the ester of the formula

followed by reacting the ester with an amine of formula NHR$^{5a}$R$^{6a}$ to obtain the amide;

(b) reacting the amide with an iodo-substituted benzyl compound of the formula

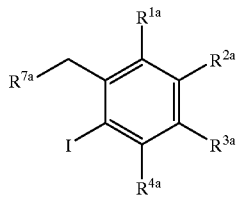

wherein R$^{1a}$, R$^{2a}$, R$^{3a}$, R$^{4a}$ and R$^{7a}$ are as defined above, in the presence of a strong base to obtain a compound of the formula

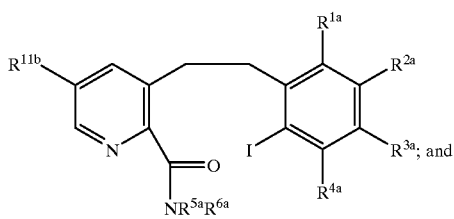

(c) cyclizing a compound of step (b) with a reagent of the formula R$^{8a}$MgL, wherein R$^{8a}$ is C$_1$–C$_8$ alkyl, aryl or heteroaryl and L is Br or Cl, provided that prior to cyclization, compounds wherein R$^{5a}$ or R$^{6a}$ is hydrogen are reacted with a suitable N-protecting group.

Compounds of Formula 1.0, wherein substituent a is NO (Ring I) and X is C or CH, can be made from compounds of Formula 13.0a using procedures well known to those skilled in the art. For example the compound of Formula 13.0a can be reacted with m-chloroperoxybenzoic acid in a suitable organic solvent, e.g., dichloromethane (usually anhydrous) or methylene chloride, at a suitable temperature, to produce a compound of Formula 13.0b

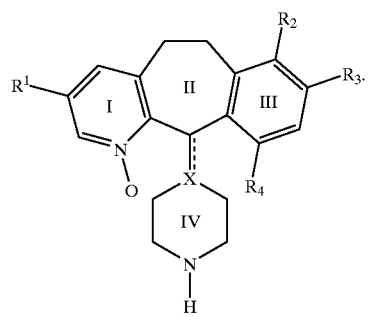

Generally, the organic solvent solution of Formula 13.0a is cooled to about 0° C. before the m-chloroperoxybenzoic acid is added. The reaction is then allowed to warm to room temperature during the reaction period. The desired product can be recovered by standard separation means. For example, the reaction mixture can be washed with an aqueous solution of a suitable base, e.g., saturated sodium bicarbonate or NaOH (e.g., 1N NaOH), and then dried over anhydrous magnesium sulfate. The solution containing the product can be concentrated in vacuo. The product can be purified by standard means, e.g., by chromatography using silica gel (e.g., flash column chromatography).

Alternatively, compounds of Formula 1.0, wherein substituent a is NO and X is C or CH, can be made from compounds of Formula 1.0, wherein substituent a is N, by the m-chloroperoxybenzoic acid oxidation procedure described above.

Also, alternatively, the compounds of Formula 1.0, wherein substituent a is NO and X is C or CH, can be made from tricyclic ketone compounds

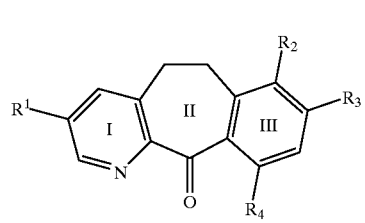

using the oxidation procedure with m-chloroperoxybenzoic acid. The oxidized intermediate compounds

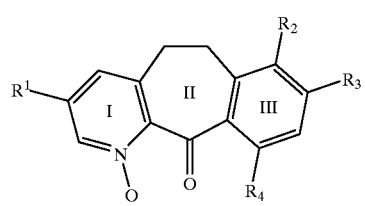

are then reacted by methods known in the art to produce compounds of the invention.

Those skilled in the art will appreciate that the oxidation reaction can be conducted on racemic mixtures and the isomers can then be separated by know techniques, or the isomers can be separated first and then oxidized to the corresponding N-oxide.

Those skilled in the art will appreciate that it is preferable to avoid an excess of m-chloroperoxybenzoic acid when the oxidation reaction is carried out on the compounds having a C-11 double bond to piperidine Ring IV. In these reactions an excess of m-chloroperoxybenzoic acid can cause epoxidation of the C-11 double bond.

(+)-Isomers of compounds of Formula 13.0a wherein X is CH can be prepared with high enantioselectivity by using a process comprising enzyme catalyzed transesterification. Preferably, a racemic compound of Formula 13.0a, wherein X is C, the double bond is present and $R^4$ is not H, is reacted with an enzyme such as Toyobo LIP-300 and an acylating agent such as trifluoroethly isobutyrate; the resultant (+)-amide is then hydrolyzed, for example by refluxing with an acid such as $H_2SO_4$, to obtain the corresponding optically enriched (+)-isomer wherein X is CH and $R^3$ is not H. Alternatively, a racemic compound of Formula 13.0a, wherein X is C, the double bond is present and $R^4$ is not H, is first reduced to the corresponding racemic compound of Formula 13.0a wherein X is CH and then treated with the enzyme (Toyobo LIP-300) and acylating agent as described above to obtain the (+)-amide, which is hydrolyzed to obtain the optically enriched (+)-isomer.

Compounds of the invention, wherein a is NO and X is N, can be prepared from the tricyclic ketone (II) described above. Ketone (II) can be converted to the corresponding C-11 hydroxy compound which in turn can be converted to the corresponding C-11 chloro compound

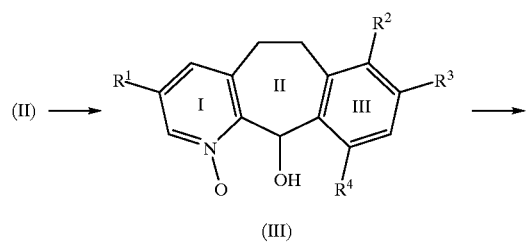

and (IV) can then be reacted with piperazine to produce the intermediate

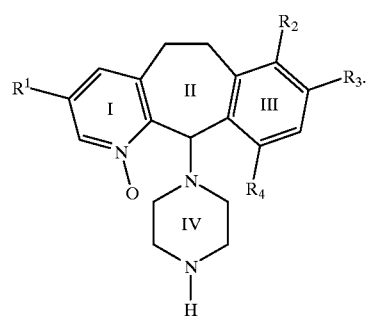

Intermediate (V) can then be reacted with the reagents, using techniques well known in the art, which will provide the desired compound.

Compounds useful in this invention are exemplified by the following examples, which should not be construed to limit the scope of the disclosure.

PREPARATIVE EXAMPLE 1

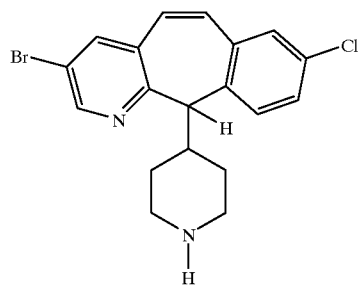

Step A:

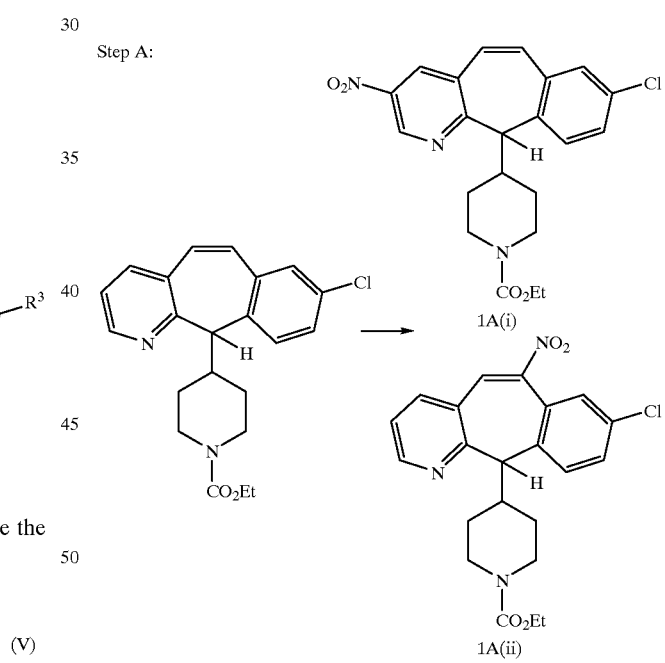

Combine 14.95 g (39 mmol) of 8-chloro-11-(1-ethoxycarbonyl-4-piperidinyl)-11H-benzo[5,6]cyclohepta[1,2-b]pyridine and 150 mL of $CH_2Cl_2$, then add 13.07 g (42.9 mmol) of $(nBu)_4NNO_3$ and cool the mixture to 0° C. Slowly add (dropwise) a solution of 6.09 mL (42.9 mmol) of TFAA in 20 mL of $CH_2Cl_2$ over 1.5 hours. Keep the mixture at 0° C. overnight, then wash successively with saturated- NaHCO₃ (aqueous), water and brine. Dry the organic solution over Na₂SO₄, concentrate in vacuo to a residue and chromatograph the residue (silica gel, EtOAc/hexane gradient) to give 4.32 g and 1.90 g of the two product compounds 1A(i) and 1A(ii), respectively. Mass Spec. for compound 1A(i): MH⁺=428.2. Mass Spec. for compound 1A(ii): MH⁺=428.3.

Step B:

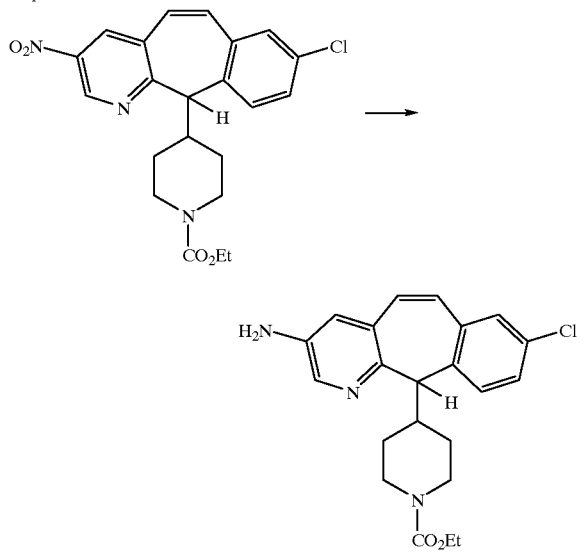

Combine 22.0 g (51.4 mmol) of the product 1A(i) from Step A, 150 mL of 85% EtOH (aqueous), 25.85 g (0.463 mole) of Fe powder and 2.42 g (21.8 mmol) of CaCl₂, and heat at reflux overnight. Add 12.4 g (0.222 mole) of Fe powder and 1.2 g (10.8 mmol) of CaCl₂ and heat at reflux for 2 hours. Add another 12.4 g (0.222 mole) of Fe powder and 1.2 g (10.8 mmol) of CaCl₂ and heat at reflux for 2 hours more. Filter the hot mixture through celite®, wash the celite® with 50 mL of hot EtOH and concentrate the filtrate in vacuo to a residue. Add 100 mL of anhydrous EtOH, concentrate to a residue and chromatograph the residue (silica gel, MeOH/CH₂Cl₂ gradient) to give 16.47 g of the product compound.

Step C:

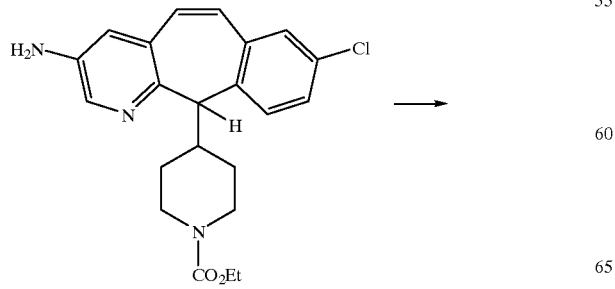

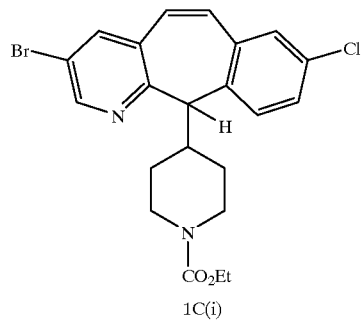

1C(i)

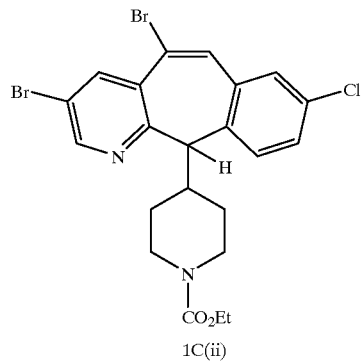

1C(ii)

Combine 16.47 g (41.4 mmol) of the product from Step B, and 150 mL of 48% HBr (aqueous) and cool to −3° C. Slowly add (dropwise) 18 mL of bromine, then slowly add (dropwise) a solution of 8.55 g (0.124 mole) of NaNO₂ in 85 mL of water. Stir for 45 minutes at −3° to 0° C., then adjust to pH=10 by adding 50% NaOH (aqueous). Extract with EtOAc, wash the extracts with brine and dry the extracts over Na₂SO₄. Concentrate to a residue and chromatograph (silica gel, EtOAc/hexane gradient) to give 10.6 g and 3.28 g of the two product compounds 1C(i) and 1C(ii), respectively. Mass Spec. for compound 1C(i): MH⁺=461.2. Mass Spec. for compound 1C(ii): MH⁺=539.

Step D:

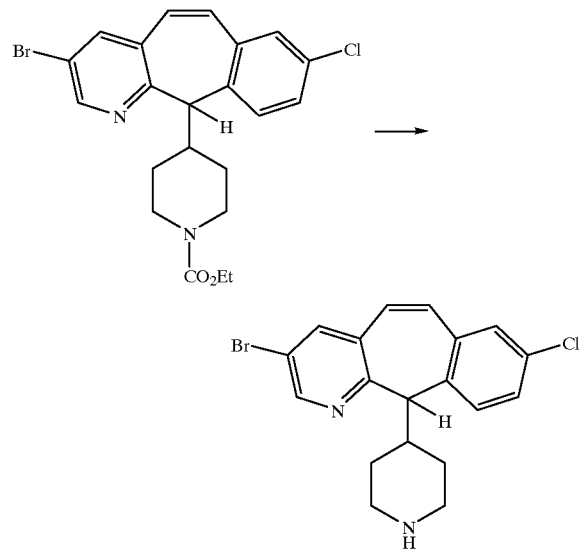

Hydrolyze the product 3C(i) of Step C by dissolving in concentrated HCl and heating to about 100° C. for @ 16 hours. Cool the mixture, the neutralize with 1 M NaOH (aqueous). Extract with CH₂Cl₂, dry the extracts over MgSO₄, filter and concentrate in vacuo to the title compound. Mass Spec.: MH⁺=466.9.

PREPARATIVE EXAMPLE 2

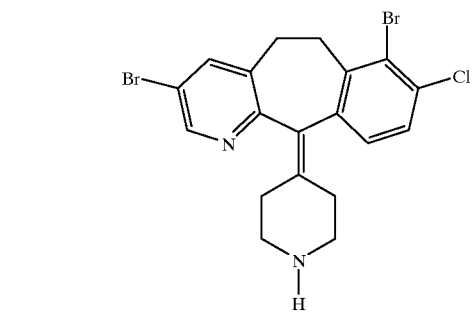

Step A:

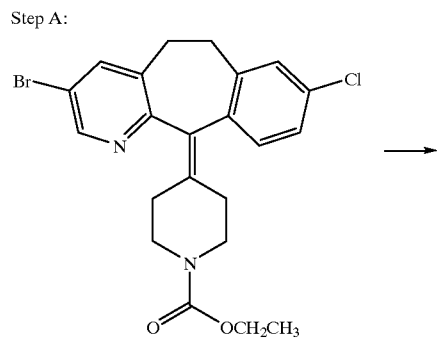

Combine 25.86 g (55.9 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 250 mL of concentrated H₂SO₄ at −5° C., then add 4.8 g (56.4 mmol) of NaNO₃ and stir for 2 hours. Pour the mixture into 600 g of ice and basify with concentrated NH₄OH (aqueous). Filter the mixture, wash with 300 mL of water, then extract with 500 mL of CH₂Cl₂. Wash the extract with 200 mL of water, dry over MgSO₄, then filter and concentrate in vacuo to a residue. Chromatograph the residue (silica gel, 10% EtOAc/CH₂Cl₂) to give 24.4 g (86% yield) of the product. m.p.=165–167° C., Mass Spec.: MH⁺=506 (CI). Elemental analysis: calculated—C, 52.13; H, 4.17; N, 8.29; found—C, 52.18; H, 4.51; N, 8.16.

Step B:

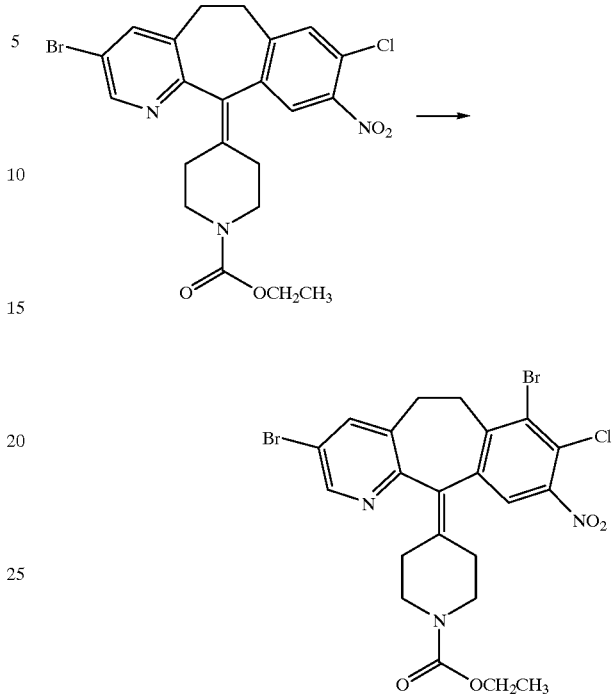

Combine 20 g (40.5 mmol) of the product of Step A and 200 mL of concentrated H₂SO₄ at 20° C., then cool the mixture to 0° C. Add 7.12 g (24.89 mmol) of 1,3-dibromo-5,5-dimethylhydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated NH₄OH (aqueous) at 0° C., and collect the resulting solid by filtration. Wash the solid with 300 mL of water, slurry in 200 mL of acetone and filter to provide 19.79 g (85.6% yield) of the product. m.p.=236–237° C., Mass Spec.: MH⁺=584 (CI). Elemental analysis: calculated—C, 45.11; H. 3.44; N, 7.17; found—C, 44.95; H, 3.57; N, 7.16

Step C:

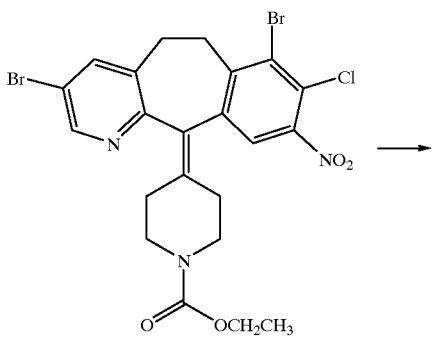

-continued

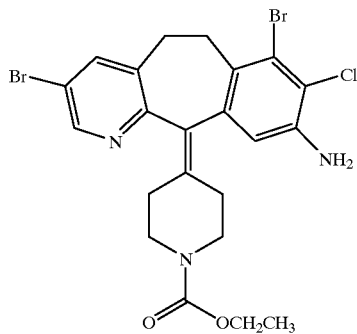

Combine 25 g (447 mmol) of Fe filings, 10 g (90 mmol) of CaCl$_2$ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of CH$_2$Cl$_2$, wash with 300 mL of water and dry over MgSO$_4$. Filter and concentrate in vacuo to a residue, then chromatograph (silica gel, 30% EtOAc/CH$_2$Cl$_2$) to give 11.4 g (60% yield) of the product. m.p.=211–212° C., Mass Spec.: MH$^+$=554 (CI). Elemental analysis: calculated—C, 47.55; H, 3.99; N, 7.56; found—C, 47.45; H, 4.31; N. 7.49.

Step D:

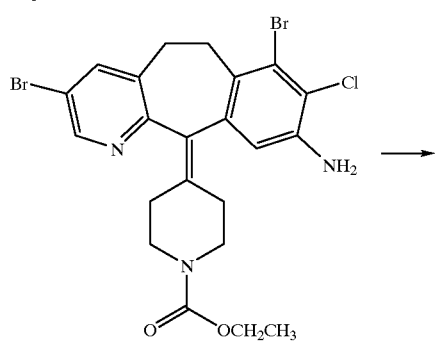

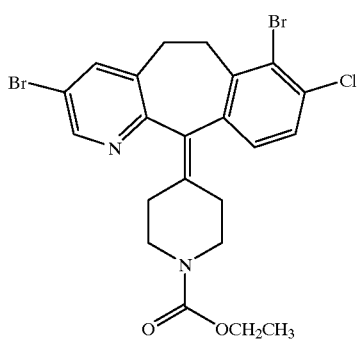

Slowly add (in portions) 20 g (35.9 mmol) of the product of Step C to a solution of 8 g (116 mmol) of NaNO$_2$ in 120 mL of concentrated HCl (aqueous) at −10° C. Stir the resulting mixture at 0° C. for 2 hours, then slowly add (dropwise) 150 mL (1.44 mole) of 50% H$_3$PO$_2$ at 0° C. over a 1 hour period. Stir at 0° C. for 3 hours, then pour into 600 g of ice and basify with concentrated NH$_4$OH (aqueous). Extract with 2×300 mL of CH$_2$Cl$_2$, dry the extracts over MgSO$_4$, then filter and concentrate in vacuo to a residue. Chromatograph the residue (silica gel, 25% EtOAc/hexanes) to give 13.67 g (70% yield) of the product. m.p.=163–165° C., Mass Spec.: MH$^+$=539 (CI). Elemental analysis: calculated—C, 48.97; H, 4.05; N, 5.22; found—C, 48.86; H, 3.91; N, 5.18.

Step E:

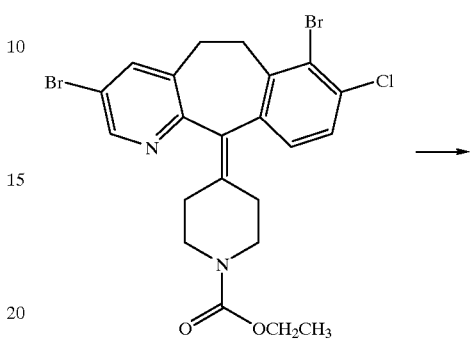

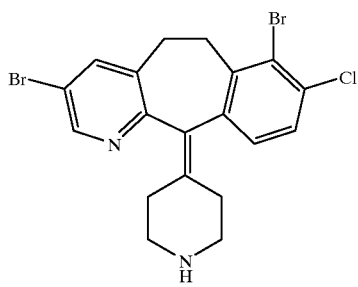

Combine 6.8 g (12.59 mmol) of the product of Step D and 100 mL of concentrated HCl (aqueous) and stir at 85° C. overnight. Cool the mixture, pour it into 300 g of ice and basify with concentrated NH$_4$OH (aqueous). Extract with 2×300 mL of CH$_2$Cl$_2$, then dry the extracts over MgSO$_4$. Filter, concentrate in vacuo to a residue, then chromatograph (silica gel, 10% MeOH/EtOAc+2% NH$_4$OH (aqueous)) to give 5.4 g (92% yield) of the title compound. m.p.= 172–174° C., Mass Spec.: MH+=467 (FAB). Elemental analysis: calculated—C, 48.69; H, 3.65; N, 5.97; found—C, 48.83; H, 3.80; N, 5.97

PREPARATIVE EXAMPLE 3

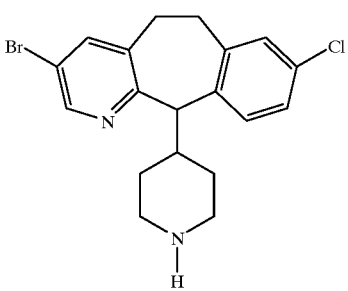

PREPARATIVE EXAMPLE 4

Step A:

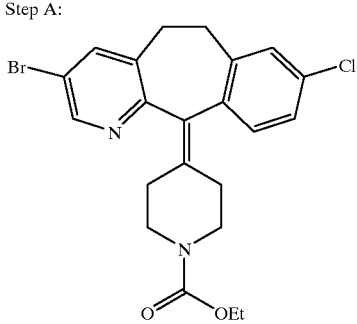

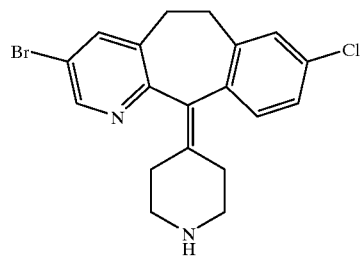

Hydrolyze 2.42 g of 4-(8-chloro-3-bromo-5,6-dihydro-11H-benzo[5,6]cyclohepta[1,2-b]pyridin-11-ylidene)-1-piperidine-1-carboxylic acid ethyl ester via substantially the same procedure as described in Preparative Example 1, Step D, to give 1.39 g (69% yield) of the product.

Step B:

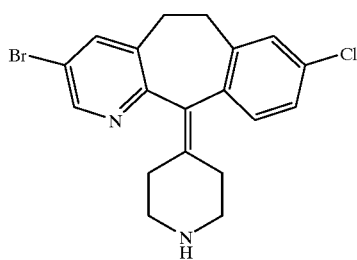

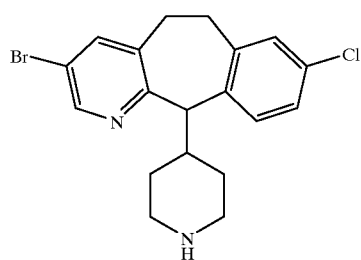

Combine 1 g (2.48 mmol) of the product of Step A and 25 mL of dry toluene, add 2.5 mL of 1 M DIBAL in toluene and heat the mixture at reflux. After 0.5 hours, add another 2.5 mL of 1 M DIBAL in toluene and heat at reflux for 1 hour. (The reaction is monitored by TLC using 50% MeOH/CH$_2$Cl$_2$+NH$_4$OH (aqueous).) Cool the mixture to room temperature, add 50 mL of 1 N HCl (aqueous) and stir for 5 min. Add 100 mL of 1 N NaOH (aqueous), then extract with EtOAc (3×150 mL). Dry the extracts over MgSO$_4$, filter and concentrate in vacuo to give 1.1 g of the title compound.

PREPARATIVE EXAMPLE 4

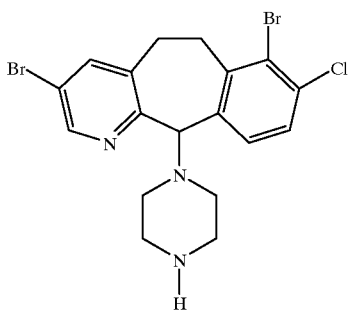

[racemic as well as (+)- and (−)-isomers]

Step A:

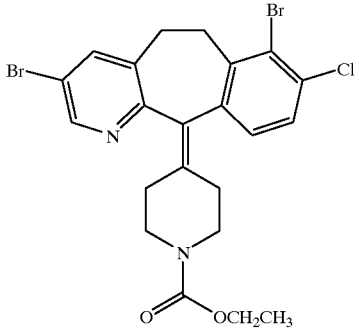

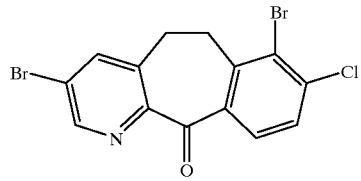

Combine 16.6 g (0.03 mole) of the product of Preparative Example 2, Step D, with a 3:1 solution of CH$_3$CN and water (212.65 mL CH$_3$CN and 70.8 mL of water) and stir the resulting slurry overnight at room temperature. Add 32.833 g (0.153 mole) of NaIO$_4$ and then 0.31 g (2.30 mmol) of RuO2 and stir at room temperature give 1.39 g (69% yield) of the product. (The addition of RuO is accompanied by an exothermnic reaction and the temperature climbs from 20° to 30° C.) Stir the mixture for 1.3 hrs. (temperature returned to 25° C. after about 30 min.), then filter to remove the solids and wash the solids with CH$_2$Cl$_2$. Concentrate the filtrate in vacuo to a residue and dissolve the residue in CH$_2$Cl$_2$. Filter to remove insoluble solids and wash the solids with CH$_2$Cl$_2$. Wash the filtrate with water, concentrate to a volume of about 200 mL and wash with bleach, then with water. Extract with 6 N HCl (aqueous). Cool the aqueous extract to 0° C. and slowly add 50% NaOH (aqueous) to adjust to pH=4 while keeping the temperature <30° C. Extract twice with CH$_2$Cl$_2$, dry over MgSO$_4$ and concentrate in vacuo to a residue. Slurry the residue in 20 mL of EtOH and cool to 0° C. Collect the resulting solids by filtration and dry the solids in vacuo to give 7.95 g of the product. $^1$H NMR (CDCl$_3$, 200 MHz): 8.7 (s, 1H); 7.85 (m, 6H); 7.5 (d, 2H); 3.45 (m, 2H); 3.15 (m, 2H).

Step B:

Combine 21.58 g (53.75 mmol) of the product of Step A and 500 mL of an anhydrous 1:1 mixture of EtOH and toluene, add 1.43 g (37.8 mmol) of $NaBH_4$ and heat the mixture at reflux for 10 min. Cool the mixture to 0° C., add 100 mL of water, then adjust to pH≈4–5 with 1 M HCl (aqueous) while keeping the temperature <10° C. Add 250 mL of EtOAc and separate the layers. Wash the organic layer with brine (3×50 mL) then dry over $Na_2SO_4$. Concentrate in vacuo to a residue (24.01 g) and chromatograph the residue (silica gel, 30% hexane/$CH_2Cl_2$) to give the product. Impure fractions were purified by rechromatography. A total of 18.57 g of the product was obtained. $^1H$ NMR (DMSO-$d_6$, 400 MHz): 8.5 (s, 1H); 7.9 (s, 1H); 7.5 (d of d, 2H); 6.2 (s, 1H); 6.1 (s, 1H); 3.5 (m, 1H); 3.4 (m, 1H); 3.2 (m, 2H).

Step C:

Combine 18.57 g (46.02 mmol) of the product of Step B and 500 mL of $CHCl_3$, then add 6.70 mL (91.2 mmol) of $SOCl_2$, and stir the mixture at room temperature for 4 hrs. Add a solution of 35.6 g (0.413 mole) of piperazine in 800 mL of THF over a period of 5 min. and stir the mixture for 1 hr. at room temperature. Heat the mixture at reflux overnight, then cool to room temperature and dilute the mixture with 1 L of $CH_2Cl_2$. Wash with water (5×200 mL), and extract the aqueous wash with $CHCl_3$ (3×100 mL). Combine all of the organic solutions, wash with brine (3×200 mL) and dry over $MgSO_4$. Concentrate in vacuo to a residue and chromatograph (silica gel, gradient of 5%, 7.5%, 10% MeOH/$CH_2Cl_2$+$NH_4OH$) to give 18.49 g of the title compound as a racemic mixture.

Step D-Separation of Enantiomers:

The racemic title compound of Step C is separated by preparative chiral chromatography (Chiralpack AD, 5 cm×50 cm column, flow rate 100 mL/min., 20% iPrOH/hexane+0.2% diethylamine), to give 9.14 g of the (+)-isomer and 9.30 g of the (−)-isomer.

Physical chemical data for (+)-isomer: m.p.=74.5°–77.5° C.; Mass Spec. $MH^+$=471.9; $[\alpha]_D^{25}$=+97.4° (8.48 mg/2 mL MeOH).

Physical chemical data for (−)-isomer: m.p.=82.9°–84.5° C.; Mass Spec. $MH^+$=471.8; $[\alpha]_D^{25}$=+97.4° (8.32 mg/2 mL MeOH).

PREPARATIVE EXAMPLE 5

Step A:

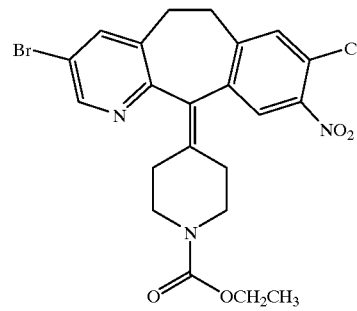

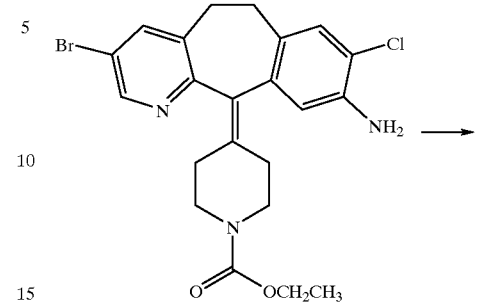

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 150 mL of concentrated $H_2SO_4$ at −5° C., then add 3.89 g (38.5 mmol) of $KNO_3$ and stir for 4 hours. Pour the mixture into 3 L of ice and basify with 50% NaOH (aqueous). Extract with $CH_2Cl_2$, dry over $MgSO_4$, then filter and concentrate in vacuo to a residue. Recrystallize the residue from acetone to give 6.69 g of the product. $^1$H NMR ($CDCl_3$, 200 MHz): 8.5 (s, 1H); 7.75 (s, 1H): 7.6 (s, 1H); 7.35 (s, 1H); 4.15 (q, 2H); 3.8 (m, 2H); 3.5-3.1 (m, 4H); 3.0-2.8 (m, 2H); 2.6-2.2 (m, 4H); 1.25 (t, 3H).

Step B:

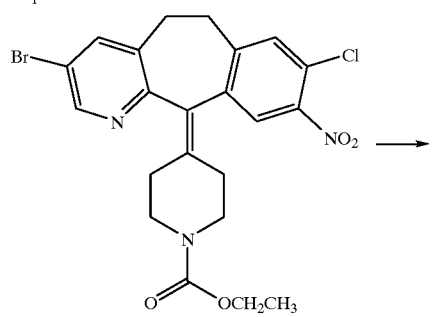

Combine 6.69 g (13.1 mmol) of the product of Step A and 100 mL of 85% EtOH/water, then add 0.66 g (5.9 mmol) of $CaCl_2$ and 6.56 g (117.9 mmol) of Fe and heat the mixture at reflux overnight. Filter the hot reaction mixture through celite® and rinse the filter cake with hot EtOH. Concentrate the filtrate in vacuo to give 7.72 g of the product. Mass Spec.: MH$^+$=478.0

Combine 7.70 g of the product of Step B and 35 mL of HOAc, then add 45 mL of a solution of $Br_2$ in HOAc and stir the mixture at room temperature overnight. Add 300 mL of 1 N NaOH (aqueous), then 75 mL of 50% NaOH (aqueous) and extract with EtOAc. Dry the extract over $MgSO_4$ and concentrate in vacuo to a residue. Chromatograph the residue (silica gel, 20%–30% EtOAc/hexane) to give 3.47 g of the product (along with another 1.28 g of partially purified product). Mass Spec.: MH$^+$=555.9.

$^1$H NMR ($CDCl_3$, 300 MHz): 8.5 (s, 1H); 7.5 (s, 1H); 7.15 (s, 1H); 4.5 (s, 2H); 4.15 (m, 3H); 3.8 (br s, 2H); 3.4-3.1 (m, 4H); 9-2.75 (m, 1H); 2.7-2.5 (m, 2H); 2.4-2.2 (m, 2H); 1.25 (m, 3H).

Step D:

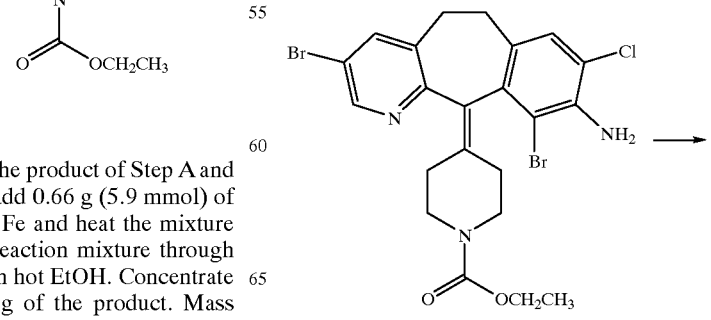

41

-continued

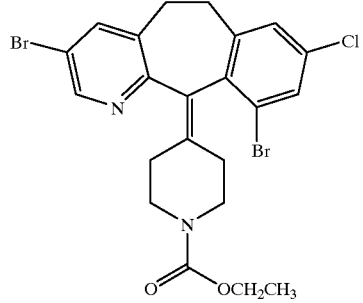

Combine 0.557 g (5.4 mmol) of t-butylnitrite and 3 mL of DMF, and heat the mixture at to 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with $CH_2Cl_2$, dry the extract over $MgSO_4$ and concentrate in vacuo to a residue. Chromatograph the residue (silica gel, 10%–20% EtOAc/hexane) to give 0.74 g of the product. Mass Spec.: $MH^+$=541.0.

$^1$H NMR (CDCl$_3$, 200 MHz): 8.52 (s, 1H); 7.5 (d, 2H); 7.2 (s, 1H); 4.15 (q, 2H); 3.9-3.7 (m, 2H); 3.5-3.1 (m, 4H); 3.0-2.5 (m, 2H); 2.4-2.2 (m, 2H); 2.1-1.9 (m, 2H); 1.26 (t, 3H).

Step E:

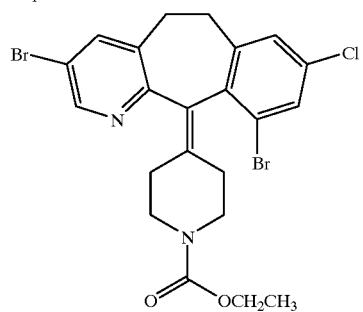

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with $CH_2Cl_2$. Dry the extract over $MgSO_4$ and concentrate in vacuo to give

42

0.59 g of the title compound. Mass Spec.: $M^+$=468.7. m.p.=123.9°–124.2° C.

PREPARATIVE EXAMPLE 6

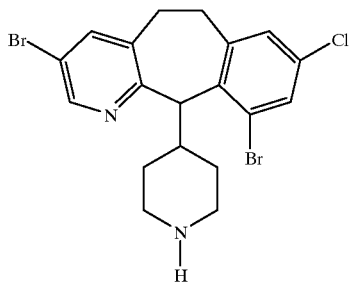

[racemic as well as (+)- and (−)-isomers]

Step A:

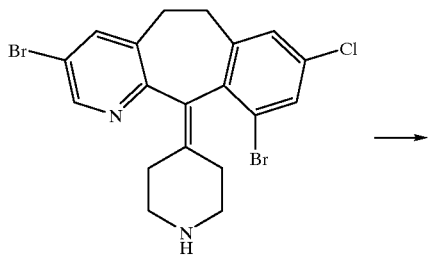

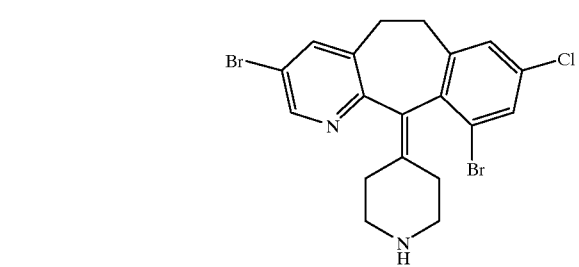

Prepare a solution of 8.1 g of the title compound from Preparative Example 5. Step E, in toluene and add 17.3 mL of a 1M solution of DIBAL in toluene. Heat the mixture at reflux and slowly add (dropwise) another 21 mL of 1 M DIBAL/toluene solution over a period of 40 min. Cool the reaction mixture to about 0° C. and add 700 mL of 1 M HCl (aqueous). Separate and discard the organic phase. Wash the aqueous phase with $CH_2Cl_2$, discard the extract, then basify the aqueous phase by adding 50% NaOH (aqueous). Extract with $CH_2Cl_2$, dry the extract over $MgSO_4$ and concentrate in vacuo to give 7.30 g of the title compound, which is a racemic mixture of enantiomers.

Step B-Separation of Enantiomers:

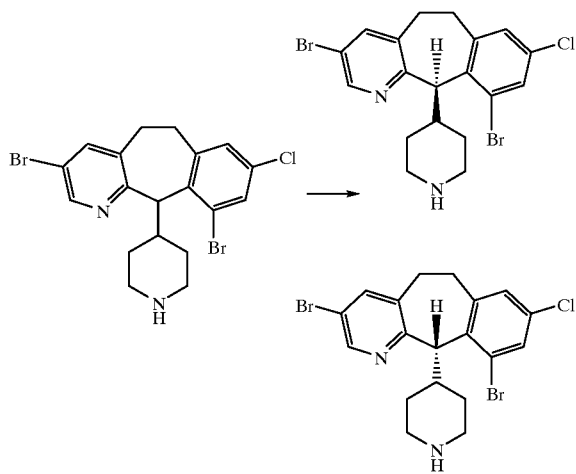

The racemic title compound of Step A is separated by preparative chiral chromatography (Chiralpack AD, 5 cm×50 cm column, using 20% iPrOH/hexane+0.2% diethylamine), to give the (+)-isomer and the (−)-isomer of the title compound.

Physical chemical data for (+)-isomer: m.p.=148.8° C.; Mass Spec. MH$^+$=469; $[\alpha]_D^{25}$=+65.6° (12.93 mg/2mL MeOH).

Physical chemical data for (−)-isomer: m.p.=112° C.; Mass Spec. MH$^+$=469; $[\alpha]_D^{25}$=−65.2° (3.65 mg/2 mL MeOH).

PREPARATIVE EXAMPLE 7

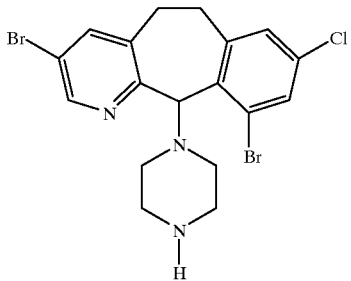

[racemic as well as (+)- and (−)-isomers]

Step A:

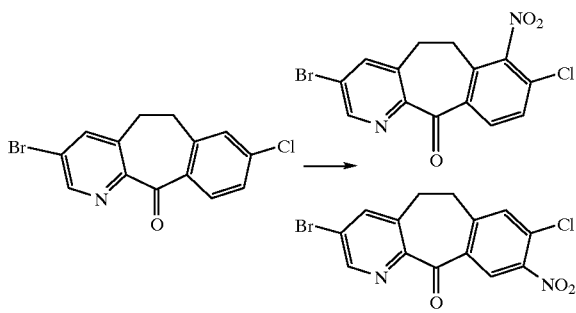

Combine 40.0 g (0.124 mole) of the starting ketone and 200 mL of $H_2SO_4$ and cool to 0° C. Slowly add 13.78 g (0.136 mole) of $KNO_3$ over a period of 1.5 hrs., then warm to room temperature and stir overnight. Work up the reaction using substantially the same procedure as described for Preparative Example 2, Step A. Chromatograph (silica gel, 20%, 30%, 40%. 50% EtOAc/hexane, then 100% EtOAc) to give 28 g of the 9-nitro product, along with a smaller quantity of the 7-nitro product and 19 g of a mixture of the 7-nitro and 9-nitro compounds.

Step B:

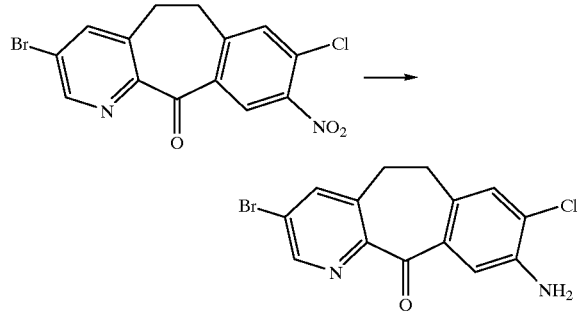

React 28 g (76.2 mmol) of the 9-nitro product of Step A, 400 mL of 85% EtOH/water, 3.8 g (34.3 mmol) of $CaCl_2$ and 38.28 g (0.685 mole) of Fe using substantially the same procedure as described for Preparative Example 2, Step C, to give 24 g of the product Step C:

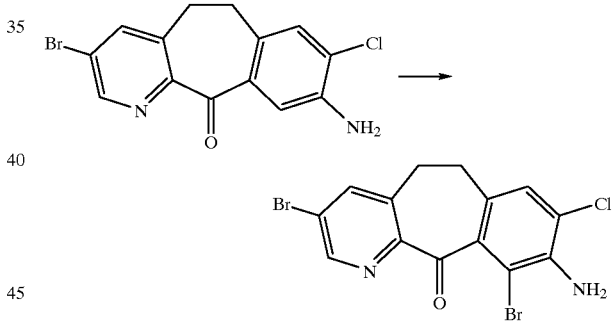

Combine 13 g (38.5 mmol) of the product of Step B, 140 mL of HOAc and slowly add a solution of 2.95 mL (57.8 mmol) of $Br_2$ in 10 mL of HOAc over a period of 20 min. Stir the reaction mixture at room temperature, then concentrate in vacuo to a residue. Add $CH_2Cl_2$ and water, then adjust to pH=8–9 with 50% NaOH (aqueous). Wash the organic phase with water, then brine and dry over $Na_2SO_4$. Concentrate in vacuo to give 11.3 g of the product.

Step D:

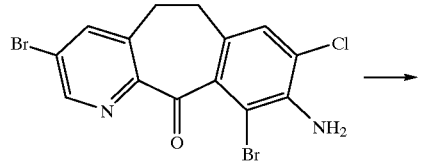

-continued

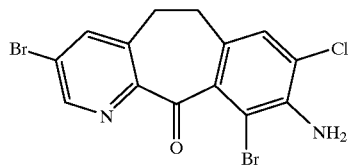

Cool 100 mL of concentrated HCl (aqueous) to 0° C., then add 5.61 g (81.4 mmol) of NaNO₂ and stir for 10 min. Slowly add (in portions) 11.3 g (27.1 mmol) of the product of Step C and stir the mixture at 0°–3° C. for 2.25 hrs. Slowly add (dropwise) 180 mL of 50% H₃PO₂ (aqueous) and allow the mixture to stand at 0° C. overnight. Slowly add (dropwise) 150 mL of 50% NaOH over 30 min., to adjust to pH=9, then extract with CH₂Cl₂. Wash the extract with water, then brine and dry over Na₂SO₄. Concentrate in vacuo to a residue and chromatograph (silica gel, 2% EtOAc/CH₂Cl₂) to give 8.6 g of the product.

Step E:

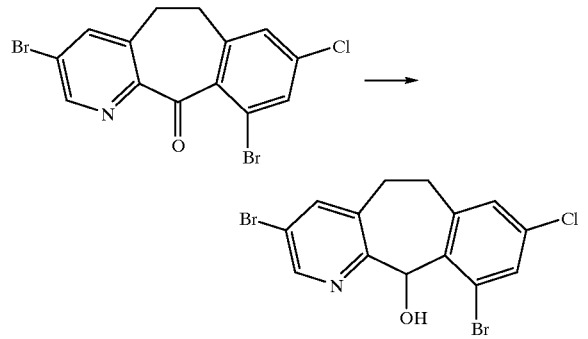

Combine 8.6 g (21.4 mmol) of the product of Step D and 300 mL of MeOH and cool to 0°–2° C. Add 1.21 g (32.1 mmol) of NaBH₄ and stir the mixture at ~0° C. for 1 hr. Add another 0.121 g (3.21 mmol) of NaBH₄, stir for 2 hr. at 0° C., then let stand overnight at 0° C. Concentrate in vacuo to a residue then partition the residue between CH₂Cl₂ and water. Separate the organic phase and concentrate in vacuo (50° C.) to give 8.2 g of the product.

Step F:

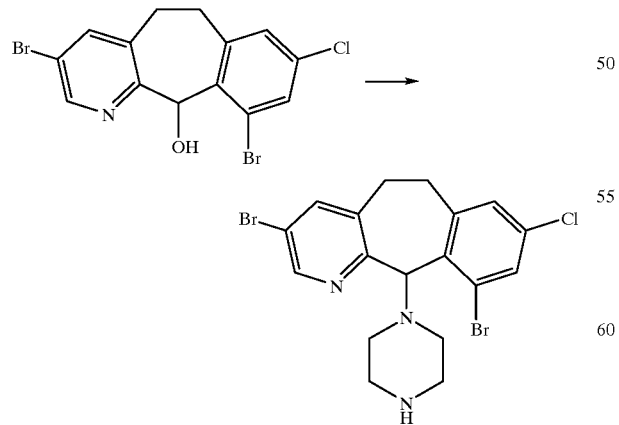

Combine 8.2 g (20.3 mmol) of the product of Step E and 160 mL of CH₂Cl₂, cool to 0° C., then slowly add (dropwise) 14.8 mL (203 mmol) of SOCl₂ over a 30 min. period. Warm the mixture to room temperature and stir for 4.5 hrs., then concentrate in vacuo to a residue, add CH₂Cl₂ and wash with 1 N NaOH (aqueous) then brine and dry over Na₂SO₄. Concentrate in vacuo to a residue, then add dry THF and 8.7 g (101 mmol) of piperazine and stir at room temperature overnight. Concentrate in vacuo to a residue, add CH₂Cl₂, and wash with 0.25 N NaOH (aqueous), water, then brine. Dry over Na₂SO₄ and concentrate in vacuo to give 9.46 g of the crude product. Chromatograph (silica gel, 5% MeOH/CH₂Cl₂+NH₃) to give 3.59 g of the title compound, as a racemate. ¹H NMR (CDCl₃, 200 MHz): 8.43 (d, 1H); 7.55 (d, 1H); 7.45 (d, 1H); 7.11 (d, 1H); 5.31 (s, 1H); 4.86-4.65 (m, 1H); 3.57-3.40 (m, 1H); 2.98-2.55 (m, 6H); 2.45-2.20 (m, 5H).

Step G-Separation of Enantiomers:

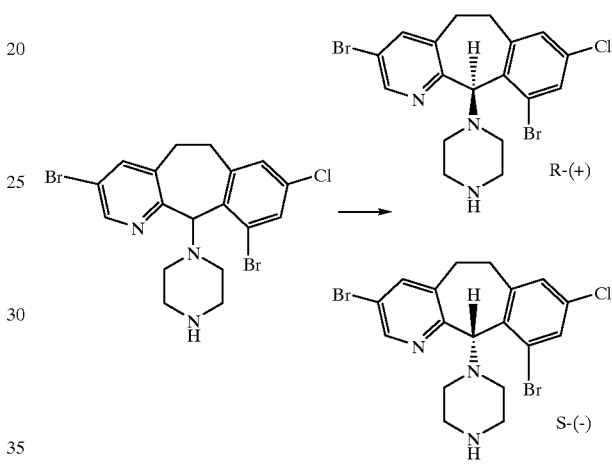

The racemic title compound from Step F (5.7 g) is chromatographed as described for Preparative Example 4, Step D, using 30% iPrOH/hexane+0.2% diethylamine, to give 2.88 g of the R-(+)-isomer and 2.77 g of the S-(−)-isomer of the title compound.

Physical chemical data for the R-(+)-isomer: Mass Spec. MH⁺=470.0; $[\alpha]_D^{25}$=+12.1° (10.9 mg/2 mL MeOH).

Physical chemical data for the S-(−)-isomer: Mass Spec. MH⁺=470.0; $[\alpha]_D^{25}$=+13.2° (11.51 mg/2 mL MeOH).

PREPARATIVE EXAMPLE 8

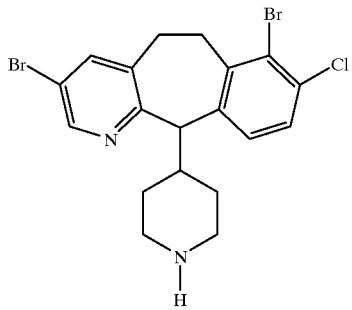

[racemic as well as (+)- and (−)-isomers]

Step A:

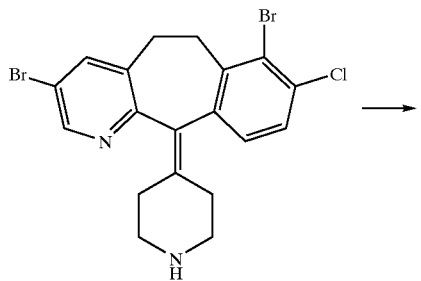

Combine 13 g (33.3 mmol) of the title compound from Preparative Example 2, Step E, and 300 mL of toluene at 20° C., then add 32.5 mL (32.5 mmol) of a 1 M solution of DIBAL in toluene. Heat the mixture at reflux for 1 hr., cool to 20° C., add another 32.5 mL of 1 M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with $CH_2Cl_2$ (3×200 mL), dry the organic layers over $MgSO_4$, then concentrate in vacuo to a residue. Chromatograph (silica gel, 12% MeOH/$CH_2Cl_2$+4% $NH_4OH$) to give 10.4 g of the title compound as a racemate. Mass Spec.: $MH^+$=469 (FAB). Partial $^1H$ NMR ($CDCl_3$, 400 MHz): 8.38 (s, 1H); 7.57 (s, 1H): 7.27 (d, 1H): 7.06 (d, 1H), 3.95 (d, 1H).

Step B-Separation of Enantiomers:

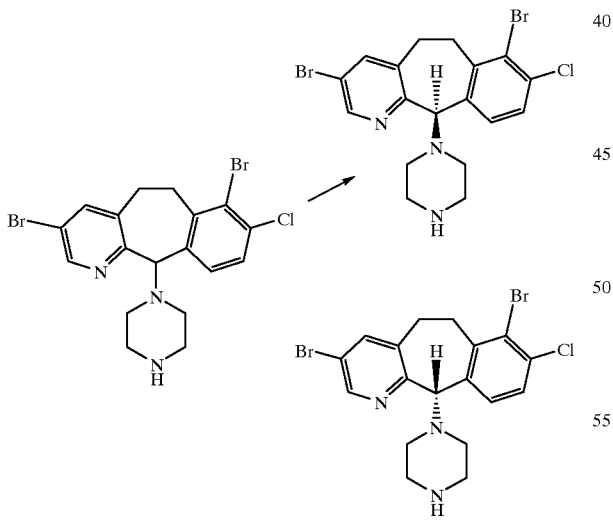

The racemic title compound of Step A is separated by preparative chiral chromatography (Chiralpack AD, 5 cm×50 cm column, using 5% iPrOH/hexane+0.2% diethylamine), to give the (+)-isomer and the (−)-isomer of the title compound.

Physical chemical data for (+)-isomer: Mass Spec. $MH^+$=469 (FAB); $[\alpha]_D^{25}$=+43.5° (c=0.402, EtOH); partial $^1H$ NMR ($CDCl_3$, 400 MHz): 8.38 (s, 1H); 7.57 (s, 1H); 7.27 (d, 1H); 7.05 (d, 1H); 3.95 (d, 1H).

Physical chemical data for (−)-isomer: Mass Spec. $MH^+$=469 (FAB); $[\alpha]_D^{25}$=−41.8° (c=0.328 EtOH); partial $^1H$ NMR ($CDCl_3$, 400 MHz): 8.38 (s, 1H); 7.57 (s, 1H); 7.27 (d, 1H); 7.05 (d, 1H); 3.95 (d, 1H).

PREPARATIVE EXAMPLE 9

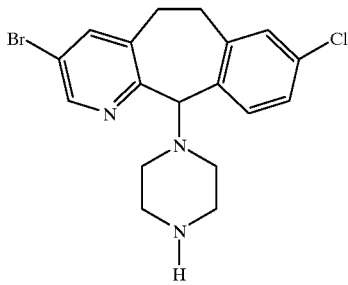

[racemic as well as R-(+)- and S-(−)-isomers]

The compound

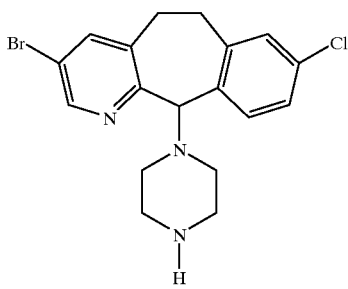

is prepared according to the procedures of Preparative Example 40 of WO 95/10516 (published Apr. 20, 1995), by following the procedures described in Example 193 of WO 95/10516.

The (+)- and (−)-isomers can be separated by following essentially the same procedure as Step D of Preparative Example 4.

Physical chemical data for the R-(+)-isomer: $^{13}C$ NMR ($CDCl_3$): 155.8 (C); 146.4 (CH); 140.5 (CH); 140.2 (C); 136.2 (C); 135.3 (C); 133.4 (C); 132.0 (CH); 129.9 (CH); 125.6 (CH); 119.3 (C); 79.1 (CH); 52.3 ($CH_2$); 52.3 ($CH_2$); 45.6 ($CH_2$); 45.6 ($CH_2$); 30.0 ($CH_2$); 29.8 ($CH_2$). $[\alpha]_D^{25}$=+25.8° (8.46 mg/2 mL MeOH).

Physical chemical data for the S-(−)-isomer: $^{13}C$ NMR ($CDCl_3$): 155.9 (C); 146.4 (CH); 140.5 (CH); 140.2 (C); 136.2 (C); 135.3 (C); 133.3 (C); 132.0 (CH); 129.9 (CH); 125.5 (CH); 119.2 (C); 79.1 (CH); 52.5 ($CH_2$); 52.5 ($CH_2$); 45.7 ($CH_2$); 45.7 ($CH_2$); 30.0 ($CH_2$); 29.8 ($CH_2$). $[\alpha]_D^{25}$=−27.9° (8.90 mg/2 mL MeOH).

PREPARATIVE EXAMPLE 10

Ethyl tetrahydropyran-4-ylidenylacetate (15.0), and ethyl 5,6-dihydro-2H-pyran-4-acetate (16.0)

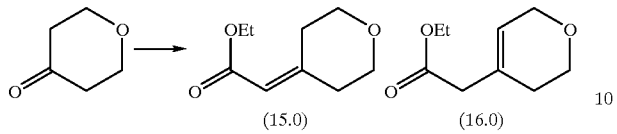

(15.0)    (16.0)

Following the chemistry described in J. Med. Chem., (1993), 36, 2300, a 2 L three-neck flask equipped with a thermometer, addition funnel and a nitrogen inlet tube and a magnetic stirrer was flame dried and charged with 1.0 L of anhydrous 1,2-dimethoxyethane and 9.0 g (0.38 mol) of sodium hydride (60% dispersion in oil). Triethyl phosphonoacetate, 56 g (0.25 mol), was added, dropwise with sirring, at such a rate that the reaction temperature was maintained at 20–25° C. After addition, the reaction was stirred at 25° C. for 45 min. then 25 g (0.25 mol) of tetrahydro-4H-pyran-4-one was added dropwise while keeping the reaction temperature at 20–25° C. by cooling with an ice bath. After addition, the reaction was refluxed for one hour, cooled to room temperature and then poured into 4 L of ice water. This was extracted with three 2 L portions of ether. The combined ether layers were dried over magnesium sulfate and concentrated under vacuum giving 27 g of a yellow oil that is a 1:1.4 mixture of 15.0 and 16.0 as determined by NMR.

Sixteen grams of the above oil were flash chromatographed on 1.5 Kg of silica gel using ethyl acetate-hexane, 10–90, and collecting 200 mL fractions. Fractions 13–22 yielded 5.65 g of pure 15.0, ethyl tetrahydropyran-4-ylidenyl-acetate, and fractions 31–50 yielded 8.06 g of pure 16.0, ethyl 5,6-dihydro-2H-pyran-4-acetate.

PREPARATIVE EXAMPLE 11

Ethyl tetrahydropyran-4-acetate

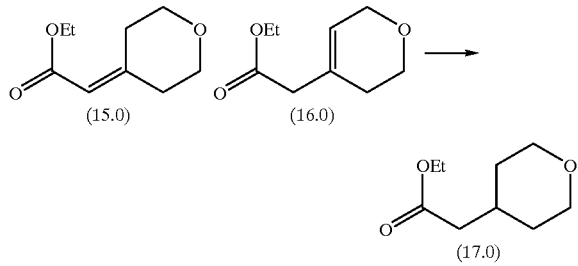

(15.0)    (16.0)

(17.0)

A mixture of 15.0 and 16.0 (3 g, 17.6 mmol) from Preparative Example 10 was dissolved in 20 mL of ethyl acetate containing 1.0 g of 10% paladium on carbon. This mixture was stirred for 18 hours under an atmosphere of hydrogen. The catalyst was filtered and the filtrate was concentrated under vacuum giving 3.04 g of the title product as a colorless oil.

PREPARATIVE EXAMPLE 12

Ethyl tetrahydrothiopyran-4-ylidenylacetate

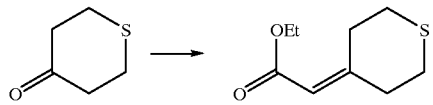

Following the procedure of Preparative Example 10, but using 2.32 g (20 mmol) of tetrahydrothiopyran-4-one instead of tetrahydropyran-4-one, 3.53 g of the product was obtained as a colorless oil.

PREPARATIVE EXAMPLE 13

Ethyl tetrahydrothiopyran-4-acetate

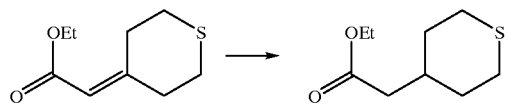

Ethyl tetrahydrothiopyran-4-ylidenylacetate (2.3 g, 12.4 mmol), from Preparative Example 12, was dissolved in 25 mL of ethanol containing 2.34 g (61.8 mmol) of sodium borohydride. After stirring for 24 hours at 25° C., an additional 1.2 g of sodium borohydride was added and the reaction was stirred for an additional 24 hours. Two additional 1.2 g portions of sodium borohydride were added followed by stirring for 24 hours after each addition. Silica gel TLC using hexane-ethyl acetate (95-5) showed the reaction to be complete. The reaction was treated with 200 mL of water and stirred for 5 minutes. The mixture was then extracted with three 150 mL portions of ethyl acetate. The combined organic layers were dried over magnesium sulfate and concentrated under vacuum giving 1.6 g of a colorless oil. The oil was chromatographed on 325 mL of silica gel using hexane-ethyl acetate (98-2) and 125 mL fractions were collected. Fractions 2–15 yielded 0.24 g of the product as a colorless oil.

PREPARATIVE EXAMPLE 14

Ethyl 2'-(1,4-dioxanyl)-acetate

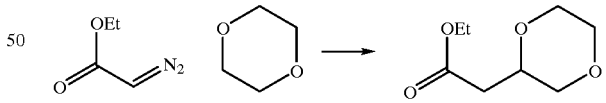

Following a procedure described in Tetrahedron (1989), 45, 69, a 125 mL three-neck flask equiped with an addition funnel, condenser and a magnetic stirrer was charged with 25 mL of anhydrous 1,4-dioxane and 0.05 g of dirhodium diacetate. This was refluxed under nitrogen and a solution of 2.0 g (17.5 mmol) of ethyl diazoacetate in 20 mL of anhydrous 1,4-dioxane was added dropwise over a period of 130 minutes. After addition was complete, the reaction was allowed to cool to 25° C. and filtered through a short pad of alumina and concentrated under vacuum. The residue was vacuum distilled (short path head) and the the fraction having a bp of 61°–68° C. at 0.5 mm Hg was collected, giving 1.5 g of the product as a colorless oil.

PREPARATIVE EXAMPLE 15

Ethyl tetrahydrofuran-2-acetate

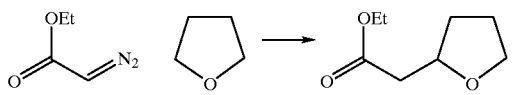

Following the procedure of Preparative Example 14, 2.0 g (17.5 mmol) of ethyl diazo acetate was reacted with tetrahydrofuran to give 1.7 g of the product as a colorless oil, bp 84°–86° C. at 20 mm Hg.

PREPARATIVE EXAMPLE 16

Ethyl tetrahydropyran-2-acetate

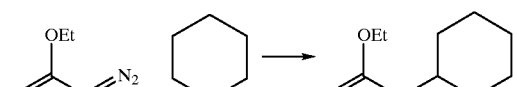

Following the procedure of Preparative Example 14, 2.0 g (17.5 mmol) of ethyl diazo acetate was reacted with tetrahydropyran to give 1.75 g of the product as a colorless oil, bp 95°–106° C. at 20 mm Hg.

PREPARATIVE EXAMPLE 17

Ethyl 2-oxabicyclo[4.1.0]heptane-7-exo-acetate (18.01 and Ethyl 2-oxabicyclo[4.1.0]heptane-7-endo-acetate (19.0)

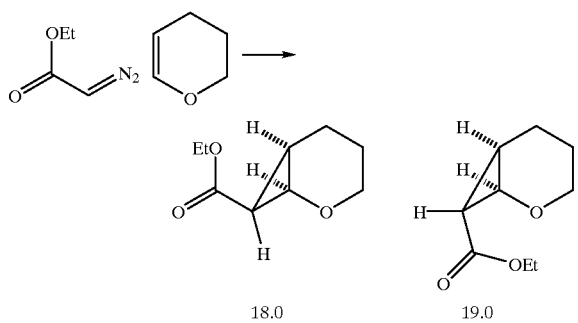

Following a procedure described in Comp. Rend. (1957), 244, 2806, a 100 mL three-neck flask equiped with an addition funnel, condenser and a magnetic stirrer was charged with 27.37 g (300 mmole) of 3,4-dihydro-2H-pyran and 0.08 g of anhydrous copper II sulfate. This was refluxed under nitrogen and a solution of 11.42 g (100 mmole) of ethyl diazo-acetate and 8.41 g (100 mmol) of 3,4-dihydro-2H-pyran was added dropwise over a 60 minute period. After addition was complete, the reaction was refluxed for an additional 2 hours and then allowed to cool to 25° C. This mixture was filtered through a short pad of alumina and concentrated under vacuum. The residue was flash chromatographed on silica gel using hexane-ethyl acetate (60-40) giving 10 g of the product as a colorless oil. Silca gel TLC Rf=0.48 using the above chromatography solvent. NMR shows a mixture of 18.0 and 19.0 in an 15% to 85% ratio.

PREPARATIVE EXAMPLE 18

Ethyl 3-oxabicyclo[3.1.0]hexane-6-exo-acetate [20.0] and Ethyl 3-oxabicyclo[3.1.0]hexane-6-endo-acetate (21.0)

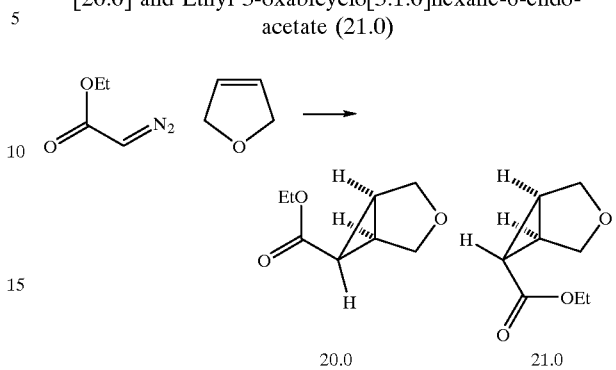

Following the procedure of Preparative Example 17, react 11.42 g (100 mmole) of ethyl diazo acetate with 2,5-dihydrofuran to give 4 g of the product as a colorless oil. Silica gel TLC Rf=0.85 (hexane-ethyl acetate 60-40).

PREPARATIVE EXAMPLE 19

Ethyl 2-oxabicyclo[3.1.0]hexane-6-exo-acetate (22.0) and Ethyl 2-oxabicyclo[3.1.0]hexane-6-endo-acetate (23.0)

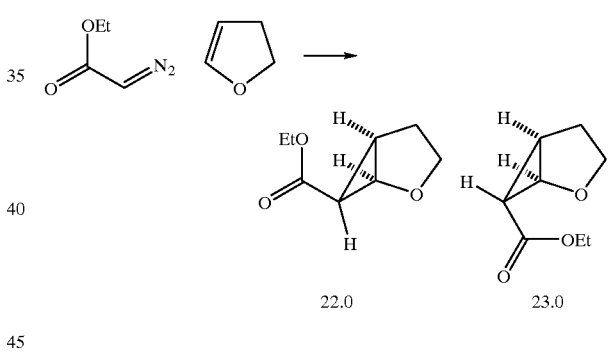

Following the procedure of Preparative Example 17, react 11.42 g (100 mmole) of ethyl diazo acetate with 2,3-dihydrofuran to give 10.4 g of the product as a colorless oil. Silica gel TLC Rf=0.91 (hexane-ethyl acetate 60-40).

PREPARATIVE EXAMPLE 20

Ethyl 4-H-pyran-4-ylidenylacetate

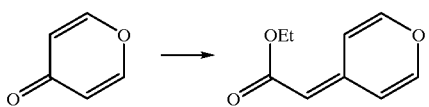

Following the procedure of Preparative Example 10 but using 5 g (52 mmol) of 4-H-pyran-4-one instead of tetrahydropyran-4-one, obtain 0.4 g of the product as a yellow solid, mp=116.5–118.7, after flash silica gel chromatography using ethyl acetate-hexane 20%–80%.

PREPARATIVE EXAMPLE 21

Ethyl tetrahydropyran-3-acetate

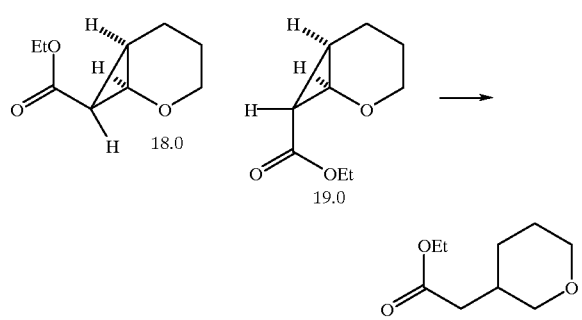

Following a procedure described in Comp. Rend. (1957), 244, 2806, if one were to hydrogenate the products of Preparative Example 17 at 750 psi and 100° C. using Raney nickle as the catalyst then one would obtain the product.

PREPARATIVE EXAMPLE 22

Ethyl tetrahydrofuran-3-acetate

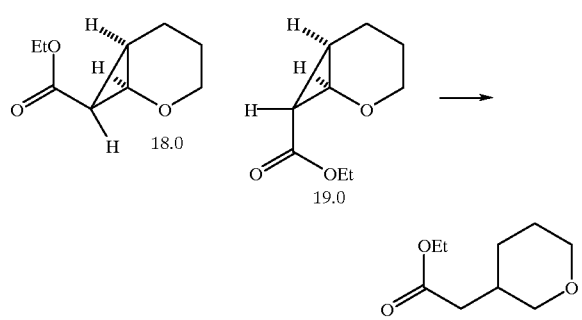

Following a procedure described in Comp. Rend. (1957), 244, 2806, if one were to hydrogenate the products of Preparative Example 19 at 750 psi and 100° C. using Raney nickle as the catalyst then one would obtain the product.

PREPARATIVE EXAMPLE 23

Ethyl 2,6-dimethyltetrahydropyran-4-ylidenylacetate

Following the procedure of Preparative Example 10, if one were to react 2,6-dimethyltetrahydro-4H-pyran-4-one (Recueil. (1959) 78, 91) with sodium hydride and triethyl phosphonoacetate to then one would obtain the product.

PREPARATIVE EXAMPLE 24

Ethyl 2,6-dimethyltetrahydropyran-4-acetate

Following the procedure of Preparative Example 11, if one were to hydrogenate the product of Preparative Example 23 one would obtain the product.

PREPARATIVE EXAMPLE 25

Ethyl 2,2,6,6-tetramethyltetrahydropyran-4-ylidenylacetate

Following the procedure of Preparative Example 10, if one were to react 2,2,6,6-tetramethyltetrahydro-4H-pyran-4-one (J. Chem. Soc. (1944) 338) with sodium hydride and triethyl phosphonoacetate then one would obtain the product.

PREPARATIVE EXAMPLE 26

Ethyl 2,2,6,6-tetramethyltetrahydropvran-4-acetate

Following the procedure of Preparative Example 11, if one were to hydrogenate the product of Preparative Example 25 one would obtain to the product.

PREPARATIVE EXAMPLE 27

Ethyl tetrahydropyran-4-acetate

Following a procedure described in Liebigs Ann. Chem. (1982) 250, if one were to react ethyl tetrahydro-4-ylidenylcarboxylate, product 15.0 of Preparative Example 10, with an excess of sodium cyanide at 80–100° C. one would obtain the product.

PREPARATIVE EXAMPLE 28

Ethyl 8-oxabicyclo[3.2.1]octa-6-ene-3-ylidenylacetate

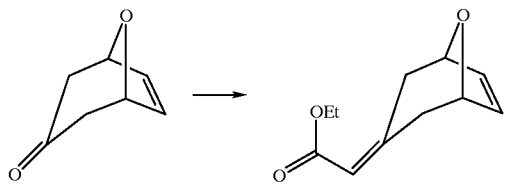

Following the procedure of Preparative Example 10, if one were to react 8-Oxabicyclo[3.2.1]octa-6-ene-3-one (J. Am. Chem. Soc. (1978) 100,1765) with sodium hydride and triethyl phosphonoacetate one would obtain the product.

PREPARATIVE EXAMPLE 29

Ethyl 8-oxabicyclo[3.2.1]octa-6-ene-3-β-acetate (24.0)

and

Ethyl 8-oxabicyclo[3.2.1]octa-6-ene-3-α-acetate (25.0)

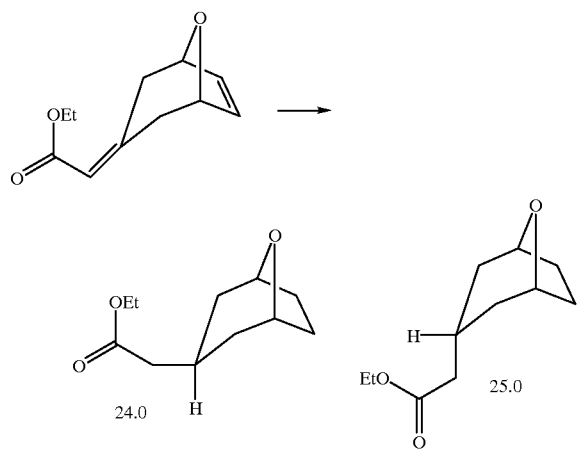

Following the procedure of Preparative Example 11, if one were to hydrogenate the product of Preparative Example 28 one would obtain the products after separation by silica gel chromatography.

PREPARATIVE EXAMPLE 30

Ethyl 2-ethoxytetrahydropyran-3-acetate

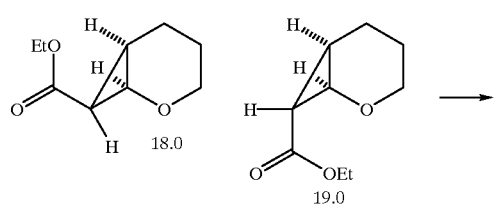

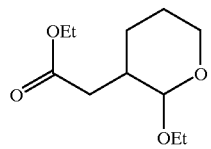

Following a procedure described in Comp. Rend. (1957), 244, 2806, if the products of Preparative Example 9 were to be reacted with boiling ethanol containing 1–2% HCl gas then the product would be obtained.

PREPARATIVE EXAMPLE 31

Ethyl 2-ethoxytetrahydrofuran-3-acetate

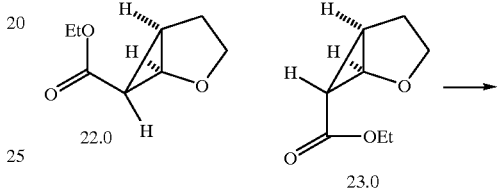

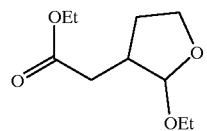

Following a procedure described in Comp. Rend. (1957), 244, 2806, if the products of Preparative Example 14 were to be reacted with boiling ethanol containing 1–2% HCl gas then the product would be obtained.

PREPARATIVE EXAMPLE 32

Tetrahydropyran-4-acetic acid

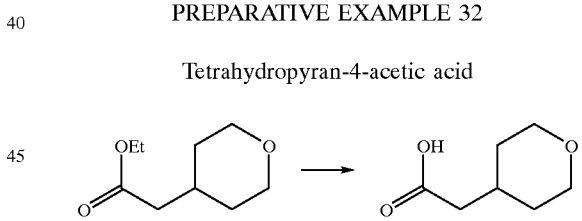

The product of Preparative Example 11 (3.04 g, 17.7 mmol) was dissoloved in 90 mL of ethanol containing 3 g (53 mmol) of potassium hydroxide. This was stirred for 18 hours and then concentrated under vacuum. The residue was dissolved in 15 mL of water, adjusted to pH 2 with 12 N HCl, and extracted with three 50 mL portions of dichloromethane. The combined organic layers were dried over magnesium sulfate and concentrated under vacuum giving 2.04 g of the product as a white solid, mp=60–63° C.

Using the hydrolysis procedure of Preparative Example 32, the esters of Preparative Examples 10–20 were hydrolyzed to the carboxylic acids identified as Preparative Examples 33 to 46 in Table 1. If one were to follow the hydrolysis procedure of Preparative Example 32, the esters of Preparative Examples 21 to 31 could be hydrolyzed to obtain the carboxylic acids identified as Preparative Examples 47–59 in Table 1.

TABLE 1

| Starting Material (Ester) | Product (Carboxylic Acid) |
|---|---|
| 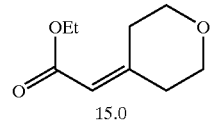 15.0 Preparative Example 10 | 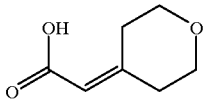 Preparative Example 33 |
| 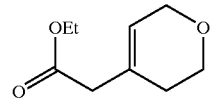 16.0 Preparative Example 10 | 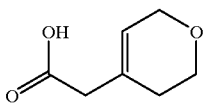 Preparative Example 34 |
| 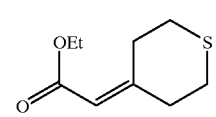 Preparative Example 12 | 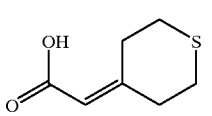 Preparative Example 35 |
| 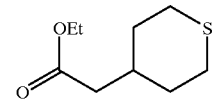 Preparative Example 13 | 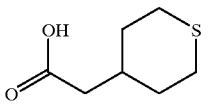 Preparative Example 36 |
| 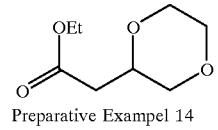 Preparative Exampel 14 | 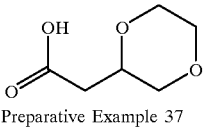 Preparative Example 37 |
| 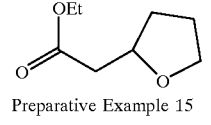 Preparative Example 15 | 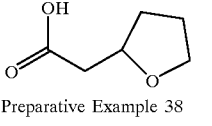 Preparative Example 38 |
| 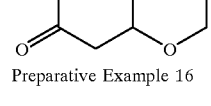 Preparative Example 16 | 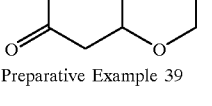 Preparative Example 39 |
| 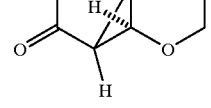 18.0 Preparative Example 17 | 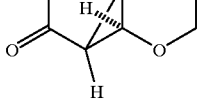 Preparative Example 40 |
| 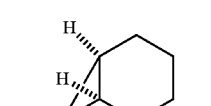 19.0 Preparative Example 17 | 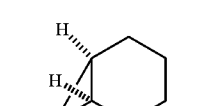 Preparative Example 41 |

TABLE 1-continued

| Starting Material (Ester) | Product (Carboxylic Acid) |
|---|---|
| 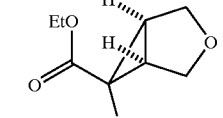 20.0 Preparative Example 18 | 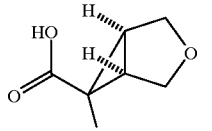 Preparative Example 42 |
| 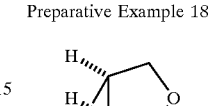 21.0 Preparative Example 18 | 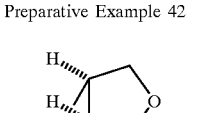 Preparative Example 43 |
| 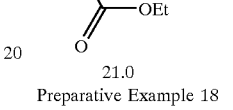 22.0 Preparative Example 19 | 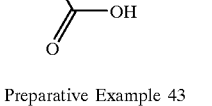 Preparative Example 44 |
| 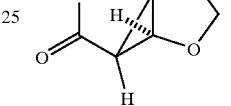 23.0 Preparative Example 19 | 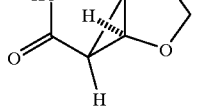 Preparative Example 45 |
| 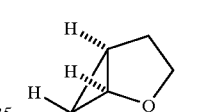 Preparative Example 20 | 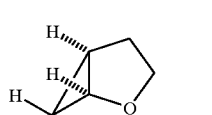 Preparative Example 46 |
| 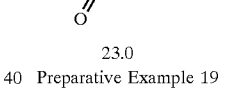 Preparative Example 21 | 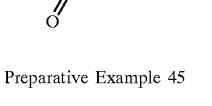 Preparative Example 47 |
| 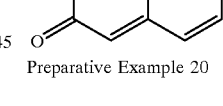 Preparative Example 22 | 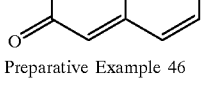 Preparative Example 48 |
| 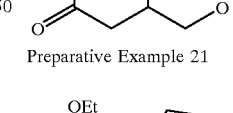 Preparative Example 23 | 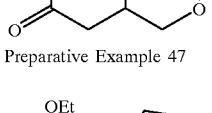 Preparative Example 49 |

TABLE 1-continued

| Starting Material (Ester) | Product (Carboxylic Acid) |
|---|---|
| Preparative Example 24 | Preparative Example 50 |
| Preparative Example 25 | Preparative Example 51 |
| Preparative Example 26 | Preparative Example 52 |
| Preparative Example 27 | Preparative Example 53 |
| Preparative Example 27 | Preparative Example 54 |
| Preparative Example 28 | Preparative Example 55 |
| Preparative Example 29 (24.0) | Preparative Example 56 |
| Preparative Example 29 (25.0) | Preparative Example 57 |
| Preparative Example 30 | Preparative Example 58 |
| Preparative Example 31 | Preparative Example 59 |

PREPARATIVE EXAMPLE 60

2-Oxabicyclo[2.2.2]-5-anti-carboxylic acid

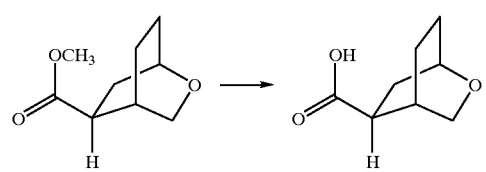

Ethyl 2-oxabicyclo[2.2.2]-5-anti-carboxylate (a by-product produced along with 5-anti-carbomethoxy-7-anti-acetoxy-2-oxabicyclo[2.2.2]octane described in Tet. Lett. (1979) 35, 3275) was hydrolyzed following the procedure of Preparative Example 32 to give the product as a waxy solid.

EXAMPLE 1

(+)-4-(3,10-Dibromo-8-chloro-6,11-dihydro-5H-benzo[5,6]cyclohepta[1,2-b]pyridine-11(R)-yl-1-[(tetrahydro-4H-pyran-4-yl)acetyl piperidine

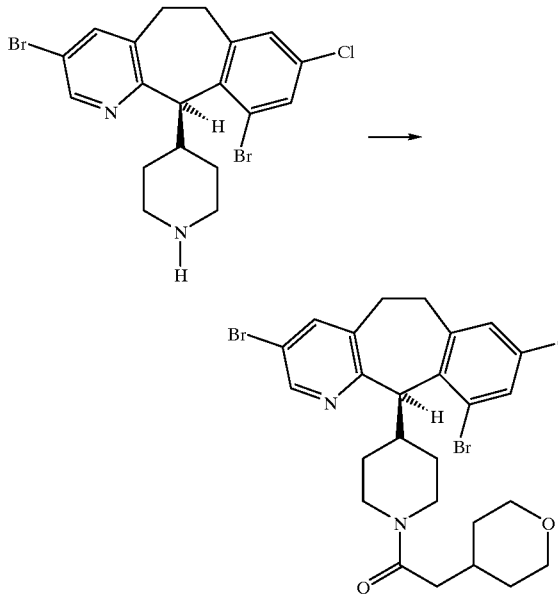

Dissolve the (+) product of Preparative Example 6, Step B, (0.1 g, 0.212 mmol) in 5 mL of DMF, stir at room temperature and add 0.043 g (0.424 mmol) of 4-methylmorpholine, 0.053 g (0.0276 mmol) of DEC, 0.037 g (0.276 mmol) of HOBT and 0.0397 g (0.276 mmole) of the product of Preparative Example 32. Stir the mixture at room temperature for 18 hours, then concentrate in vacuo to a residue and partition between methylene chloride and water. Wash the organic phase with aqueous sodium bicarbonate solution then brine. Dry the organic phase over magnesium sulfate, filter and concentrate in vacuo to a residue. Chromatograph the residue on a silica gel plate, eluting with methylene chloride-methanol (96%-4%) to yield the product (0.13 g) as a white solid. M.p.=83.2–88.7° C., Mass Spec.: MH+=597. $[\alpha]_D^{23.2°\ C.}$=+55.5°, c=0.2, methylene chloride.

Using the coupling procedure of Example 1, the acids of Preparative Examples 33–60 are reacted with the (+) product of Preparative Example 6, Step B, to produce the compounds of Formula 1.16:

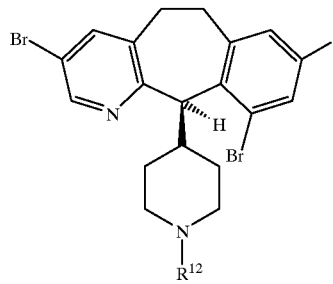

(1.16)

wherein $R^{12}$ is as defined in Table 2 below. In Table 2, "EX" stands for Example, and "mp" stands for melting point:

TABLE 2

| EX | $R^{12}$ | mp (° C.) |
|---|---|---|
| 1 | | 83.2–88.7 |
| 2 | | 103.3–107.9 |
| 3 | | 110.3–113.9 |
| 4 | | — |
| 5 | | 115.9–119.9 |
| 6 | | 111–124 (d) |
| 7 | | 107–115 (d) |
| 8 | | 116–122 (d) |
| 9 | | 125.8–127.3 |
| 10 | | — |
| 11 | | 124.9–127.8 |

TABLE 2-continued

| EX | R¹² | mp (° C.) |
|---|---|---|
| 12 | | — |
| 13 | | 124.3–125.3 |
| 14 | | — |
| 15 | | 174.3–178.8 |
| 16 | | — |
| 17 | | — |
| 18 | | — |
| 19 | | — |
| 20 | | — |
| 21 | | — |
| 22 | | — |
| 23 | | — |
| 24 | | — |
| 25 | | — |
| 26 | | — |
| 27 | | — |
| 28 | | — |

TABLE 2-continued

| EX | R12 | mp (° C.) |
|---|---|---|
| 29 | Isomer 1 | 152–164 (d) |
| 30 | Isomer 2 | 151–159 (d) |
| 31 | Starting acid is commerically available | 118.1–122.3 |
| 32 | Starting acid described in J. Am. Chem. Soc (1995) 115, 8401 | — |

EXAMPLE 33

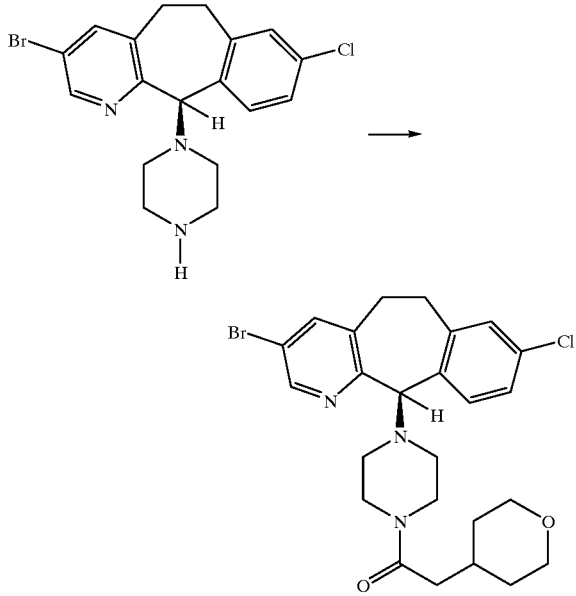

Following the procedure of Example 1, react the R-(+)-isomer of Preparative Example 9 with the product of Preparative Example 32 to give the product as a white solid mp=93.5–97.6° C.

EXAMPLE 34

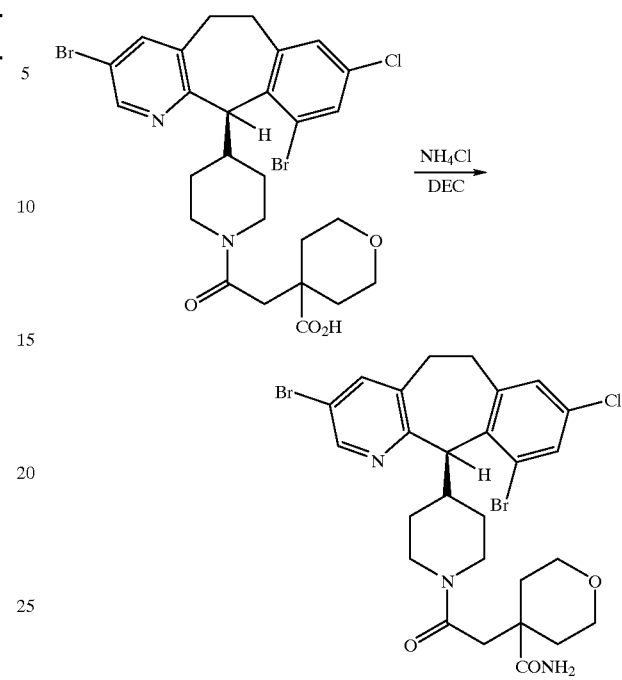

If the the coupling procedure described in Example 1 were to be used, the product of Example 23 could be reacted with ammonium chloride to produce the product.

EXAMPLE 35

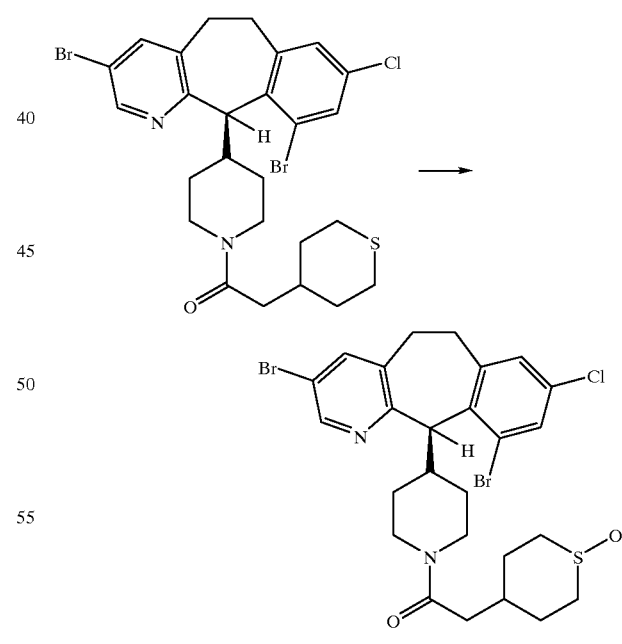

Dissolve 90 mg (0.14 mmol) of the product of Example 5 in 5 mL of THF and 34 mL of trifluoroacetic acid. Add 37 mL of 30% hydrogen peroxide and stir for three days. Concentrate under vacuum and partition the residue between water and dichloromethane. Dry the organic layer over magnesium sulfate, concentrate under vacuum and chromatograph the residue by preparative silica gel TLC using dichloromethane saturated with ammonia to give the product as a white solid. M.p.=135.6–140° C., Mass Spec.: MH+= 628.

EXAMPLE 36

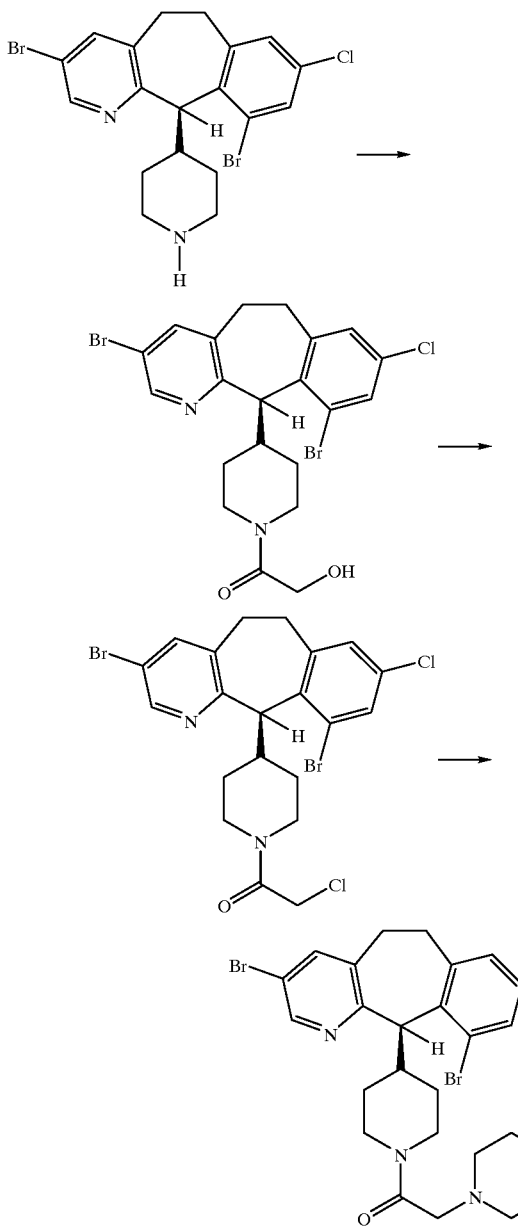

Dissolve the (+) product of Preparative Example 6, Step B (0.5 g, 1.06 mmol) in 10 mL of dichloromethane, stir at room temperature and add 0.128 g (1.27 mmol) of 4-methylmorpholine, 0.285 g (1.48 mmol) of DEC, 0.172 g (1.27 mmol) of HOBT and 0.097 g (1.27 mmole) of glycolic acid. Stir the mixture at room temperature for 18 hours, then concentrate in vacuo to a residue and partition between methylene chloride and water. Wash the organic phase with aqueous sodium bicarbonate solution then brine. Dry the organic phase over magnesium sulfate, filter and concentrate in vacuo to a residue. Chromatograph the residue by preparative silica gel TLC, eluting with methylene chloride-methanol (95%-5%) to yield the amide of glycolic acid and the starting tricyclic reactant of Preparative Example 6.

Step B

Dissolve 0.34 g (0.643 mmol) of the product of Step A in 1 mL of dichloromethane containing 5.4 mL of thionyl chloride. Allow to stir for 18 hours and concentrate under vacuum. Add 10 mL of toluene to the residue and concentrate under vacuum and repeat this step two additional times to give the product.

Step C

Dissolve the product of Step B in 1.0 mL of dichloromethane followed by 0.124 g of morpholine. Stir for 18 hours then concentrate under vacuum. Partition the residue between dichloromethane and aqueous sodium bicarbonate solution. Concentrate the organic layer under vacuum and chromatograph the residue by preparative silica gel TLC using methylene chloride-methanol (95%-5%) to yield the product as a white solid. M.p=112.4–113.5° C., Mass. Spec.: MH+=599.

EXAMPLE 37

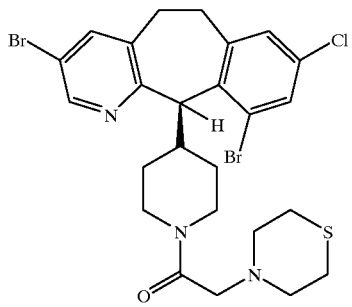

Following the procedure of Example 36, thiomorpholine was used instead of morpholine in Step C to yield the product as a white solid.

EXAMPLE 38

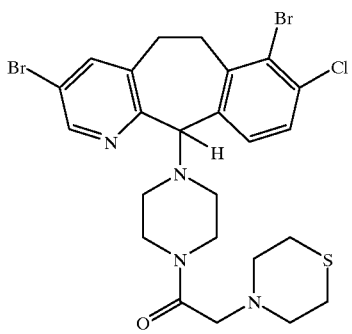

Following the procedure of Example 36, except in Step A the (−) product of Preparative Example 4 Step D was used instead of the (+) product of Preparative Example 6, Step B, and thiomorpholine was used instead of morpholine in Step C, to yield the product as a white solid.

EXAMPLE 39

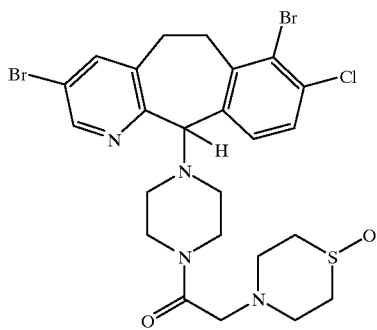

The product of Example 38 was reacted under the conditions of Example 35 to yield the product as a white solid.

EXAMPLE 40

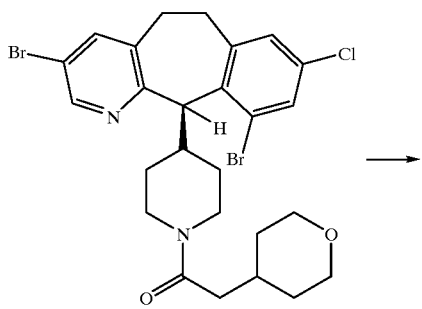

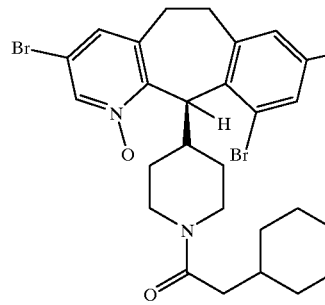

Dissolve 160 mg (0.268 mmol) of the product of Example 1 in 3 mL of $CH_2Cl_2$ and add 162.3 mg (0.536 mmol) of 4-chloroperoxybenzoic acid (57% pure) and stir for 3 hr. Dilute with 50 mL of $CH_2Cl_2$ then wash with saturated $NaHCO_3$ followed by brine. Dry the organic layer over $MgSO_4$, concentrate in vacuo and purify the residue by preparative silica gel TLC using 2% methanol in $CH_2Cl_2$ saturated with ammonia to give 116 mg (71%) of the title compound as a white solid. m.p.=141–151° C. (dec); MS MH+=613.

ASSAYS

FPT $IC_{50}$ (inhibition of farnesyl protein transferase, in vitro enzyme assay) and COS Cell $IC_{50}$ (Cell-Based Assay) were determined following the assay procedures described in WO 95/10516, published Apr. 20, 1995. GGPIT $IC_{50}$ (inhibition of geranylgeranyl protein transferase, in vitro enzyme assay), Cell Mat Assay, and anti-tumor activity (in vivo anti-tumor studies) could be determined by the assay procedures described in WO 95/10516. The disclosure of WO 95/10516 is incorporated herein by reference thereto.

Additional assays can be carried out by following essentially the same procedure as described above, but with substitution of alternative indicator tumor cell lines in place of the T24-BAG cells. The assays can be conducted using either DLD-1-BAG human colon carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay:

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of farnesyl transferase inhibitor as the top layer. After the top layer is solidified, plates can be incubated for 10–16 days at 37° C. under 5% $CO_2$ to allow colony outgrowth. After incubation, the colonies can be stained by overlaying the agar with a solution of MTT (3-[4,5-dimethylthiazol-2-yl]-2,5-diphenyltetrazolium bromide, Thiazolyl blue) (1 mg/mL in PBS). Colonies can be counted and the $IC_{50}$'s can be determined.

The results are given in Table 3. In Table 3, "nM" represents nanomolar.

TABLE 3

| Compound of Example No. | FPT $IC_{50}$ (nM) | COS Cell $IC_{50}$ (nM) |
| --- | --- | --- |
| 1 | 0.4 | 1.8 |
|  | 1.2 | 12 |
|  | 2.4 | 15 |
| 2 | 5.5 | 285 |
| 3 | 6.1 | — |
| 5 | 3.5 | 143 |
| 6 | 23 | — |
| 7 | 42 | — |
| 8 | 2.0 | 68 |
| 29 | 6.7 | 30 |
| 30 | 7.5 | 75 |
| 33 | 45 | — |
| 35 | 2.3 | — |
| 36 | 3.1 | — |
| 37 | 4.9 | <10 |
| 39 | 4.7 | 68 |
| 40 | 2.2 | 100% @ 10 |

The compound of Example 40 had a Soft Agar $IC_{50}$ of 8 nM.

For preparing pharmaceutical compositions from the compounds described by this invention, inert, pharmaceutically acceptable carriers can be either solid or liquid. Solid form preparations include powders, tablets, dispersible granules. capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

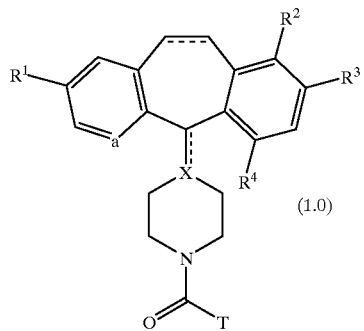

(1.0)

or a pharmaceutically acceptable salt or solvate thereof, wherein:
a represents N or NO⁻;
$R^1$ and $R^3$ are the same or different halo atom;
$R^2$ and $R^4$ are selected from H and halo, provided that at least one of $R^2$ and $R^4$ is H;
the dotted line (---) represents an optional bond;
X is N, and the optional bond to X is absent;
T is a substituent selected from:

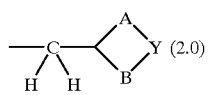

(2.0)

wherein:
A represents —(CH$_2$)$_b$—;
B represents —(CH$_2$)$_d$—;
b and d are independently selected from: 0, 1, 2, 3, or 4 such that the sum of b and d is 3 or 4; and
Y is selected from: O, S, SO, or SO$_2$;

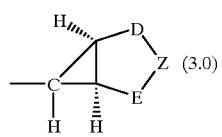

(3.0)

wherein:
D represents —(CH$_2$)$_e$—;
E represents —(CH$_2$)$_f$—;
e and f are independently selected from: 0, 1, 2, or 3 such that the sum of e and f is 2 or 3; and
Z is O;

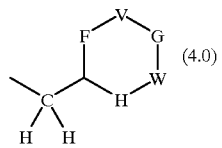

(4.0)

wherein:
F represents —(CH$_2$)$_g$—;
G represents —(CH$_2$)$_h$—;
U represents —(CH$_2$)$_i$—;
h represents 1, 2, or 3;
g and i are independently selected from: 0, 1 or 2 such that the sum of h, g and i is 2 or 3; and
V and W are independently selected from O, S, SO, or SO$_2$;

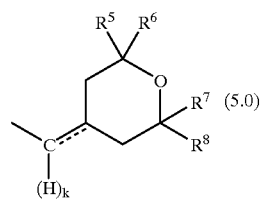

(5.0)

wherein:
the dotted line (---) represents an optional bound;
k is 1 or 2 such that when the optional bond is present k represents 1, and when the optional double bond is absent then k represents 2;
$R^5$, $R^6$, $R^7$ and $R^8$ are the same alkyl or
$R^5$ and $R^7$ are the same alkyl and
$R^6$ and $R^8$ are H;

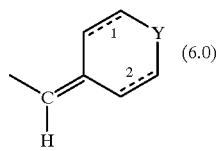

(6.0)

wherein:
the dotted lines (---) represent optional bonds 1 and 2 such that optional bonds 1 and 2 are both present, or optional bonds 1 and 2 are both absent;
Y represents O, S, SO, or SO$_2$;

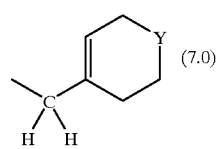

(7.0)

wherein:
Y represents O, S, SO, or SO$_2$;

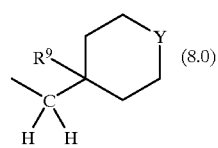

(8.0)

wherein:

$R^9$ is selected from: —CN, —CO$_2$H, or —C(O)N(R$^{10}$)$_2$;
Y represents O;
each $R^{10}$ is the same or diferent alkyl group;

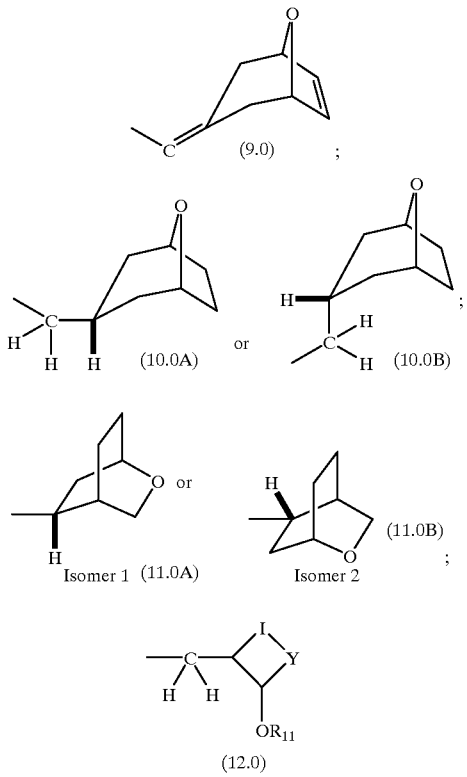

wherein:

I represents —(CH$_2$)$_m$—;
m represents 2 or 3;
Y represents O, S, SO, or SO$_2$; and
$R^{11}$ represents alkyl.

2. The compound of claim 1 having the formula:

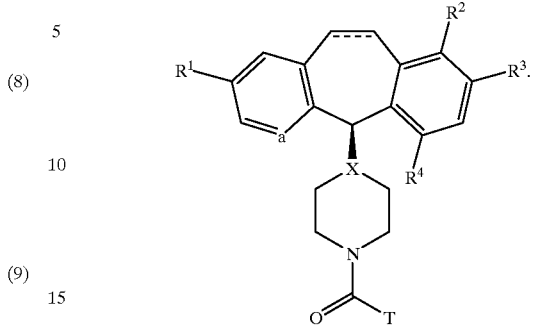

(1.3)

3. The compound of claim 1 wherein $R^1$ is halo, $R^2$ is H, $R^3$ is halo, and $R^4$ is H.

4. The compound of claim 3 wherein $R^1$ is Br and $R^3$ is Cl.

5. The compound of claim 4 wherein X is CH, a is N, and the C5–C6 double bond is absent.

6. The compound of claim 1 wherein $R^1$ is halo, $R^2$ is halo, $R^3$ is halo, and $R^4$ is H; or $R^1$ is halo, $R^2$ is H, $R^3$ is halo, and $R^4$ is halo.

7. A method of treating tumor cells wherein the tumor cells treated are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumor cells, breast tumor cells or prostate tumor cells by inhibition of farnesyl protein transferase, comprising the administration to a human in need thereof an effective amount of a compound of claim 1.

8. A method of inhibiting farnesyl protein transferase in a human comprising the administration to a human in need thereof an effective amount of a compound of claim 1.

9. A pharmaceutical composition comprising a compound of claim 1 in combination with a pharmaceutically acceptable carrier.

* * * * *